United States Patent
Wenchell et al.

(10) Patent No.: US 8,591,466 B2
(45) Date of Patent: Nov. 26, 2013

(54) APPARATUS AND METHOD FOR PROVIDING PERCUTANEOUS ACCESS AND MEDICAMENT TO A TARGET SURGICAL SITE

(75) Inventors: Thomas Wenchell, Durham, CT (US);
Robert C. Smith, Middletown, CT (US)

(73) Assignee: Covidien LP, Mansfield, MA (US)

( * ) Notice: Subject to any disclaimer, the term of this patent is extended or adjusted under 35 U.S.C. 154(b) by 936 days.

(21) Appl. No.: 12/266,758

(22) Filed: Nov. 7, 2008

(65) Prior Publication Data

US 2009/0287147 A1 Nov. 19, 2009

Related U.S. Application Data

(62) Division of application No. 10/484,749, filed as application No. PCT/US02/24308 on Jul. 31, 2002, now Pat. No. 7,449,011.

(60) Provisional application No. 60/309,252, filed on Aug. 1, 2001.

(51) Int. Cl.
*A61M 5/178* (2006.01)
*A61M 29/00* (2006.01)

(52) U.S. Cl.
USPC ............ 604/164.03; 604/164.01; 604/164.02; 604/164.1; 604/164.11; 604/99.04

(58) Field of Classification Search
USPC ............ 604/43, 104, 191, 264, 99.04, 164.1, 604/164.01–164.03; 606/191
See application file for complete search history.

(56) References Cited

U.S. PATENT DOCUMENTS

| | | | |
|---|---|---|---|
| 668,879 | A | 2/1901 | Miller |
| 1,213,001 | A | 1/1917 | Philips |
| 1,248,492 | A | 12/1917 | Hill |
| 2,548,602 | A | 4/1951 | Greenburg |
| 3,509,883 | A | 5/1970 | Dibelius |
| 3,545,443 | A | 12/1970 | Ansari |

(Continued)

FOREIGN PATENT DOCUMENTS

| | | |
|---|---|---|
| DE | 198 14 576 | 10/1999 |
| EP | 0 177 177 | 4/1986 |

(Continued)

OTHER PUBLICATIONS

Product Brochure Endomed, Cooper Surgical, Inc. (1992) (2 pages).

(Continued)

*Primary Examiner* — Emily Schmidt
*Assistant Examiner* — Bradley G Thomas, Jr.

(57) ABSTRACT

A method of forming and enlarging a percutaneous penetration is provided. The method includes the step of providing a radially expandable dilation assembly having a needle assembly removably inserted in a axial lumen thereof. The radially expandable dilation assembly includes a radially expandable sleeve body defining a lumen and an introducer seal disposed across the lumen and defining an opening formed therein. The method further includes the steps of penetrating the radially expandable dilation assembly and needle assembly through tissue to a target surgical site, withdrawing the needle assembly from the radially expandable dilation assembly, and inserting an expansion assembly through the opening formed in the introducer seal and into the axial lumen of the radially expandable dilation assembly.

11 Claims, 24 Drawing Sheets

(56) References Cited

U.S. PATENT DOCUMENTS

| | | | |
|---|---|---|---|
| 3,742,958 | A | 7/1973 | Rundles |
| 3,788,318 | A | 1/1974 | Kim et al. |
| 3,789,852 | A | 2/1974 | Kim et al. |
| 3,902,492 | A | 9/1975 | Greenhalgh |
| 4,018,230 | A | 4/1977 | Ochiai et al. |
| 4,141,364 | A | 2/1979 | Schultze |
| 4,411,655 | A | 10/1983 | Schreck |
| 4,447,237 | A | 5/1984 | Frisch et al. |
| 4,479,497 | A | 10/1984 | Fogarty et al. |
| 4,581,025 | A | 4/1986 | Timmermans |
| 4,589,868 | A | 5/1986 | Dretler |
| 4,601,713 | A | 7/1986 | Fuqua |
| 4,610,688 | A | 9/1986 | Silvestrini et al. |
| 4,650,466 | A | 3/1987 | Luther |
| 4,710,181 | A | 12/1987 | Fuqua |
| 4,716,901 | A | 1/1988 | Jackson et al. |
| 4,738,666 | A | 4/1988 | Fuqua |
| 4,739,762 | A | 4/1988 | Palmaz |
| 4,753,636 | A | 6/1988 | Free |
| 4,762,128 | A | 8/1988 | Rosenbluth |
| 4,772,266 | A | 9/1988 | Groshong |
| 4,798,193 | A | 1/1989 | Giesy et al. |
| 4,846,791 | A * | 7/1989 | Hattler et al. ............... 604/43 |
| 4,865,593 | A | 9/1989 | Ogawa et al. |
| 4,869,717 | A | 9/1989 | Adair |
| 4,888,000 | A | 12/1989 | McQuilkin et al. |
| 4,896,669 | A | 1/1990 | Bhate et al. |
| 4,899,729 | A | 2/1990 | Gill et al. |
| 4,921,479 | A | 5/1990 | Grayzel |
| 4,941,874 | A | 7/1990 | Sandow et al. |
| 4,954,126 | A | 9/1990 | Wallsten |
| 4,955,895 | A | 9/1990 | Sugiyama et al. |
| 4,972,827 | A | 11/1990 | Kishi et al. |
| 4,986,830 | A | 1/1991 | Owens et al. |
| 5,021,241 | A | 6/1991 | Yamahira et al. |
| 5,045,056 | A | 9/1991 | Behl |
| 5,078,736 | A | 1/1992 | Behl |
| 5,100,388 | A | 3/1992 | Behl et al. |
| 5,104,382 | A | 4/1992 | Brinkerhoff et al. |
| 5,112,304 | A | 5/1992 | Barlow et al. |
| 5,116,318 | A | 5/1992 | Hillstead |
| 5,122,122 | A | 6/1992 | Allgood |
| 5,139,511 | A | 8/1992 | Gill et al. |
| 5,158,545 | A | 10/1992 | Trudell et al. |
| 5,183,464 | A | 2/1993 | Dubrul et al. |
| 5,188,602 | A | 2/1993 | Nichols |
| 5,201,756 | A | 4/1993 | Horzewski et al. |
| 5,222,938 | A | 6/1993 | Behl |
| 5,222,971 | A | 6/1993 | Willard et al. |
| 5,234,425 | A | 8/1993 | Fogarty et al. |
| 5,246,424 | A | 9/1993 | Wilk |
| 5,250,025 | A | 10/1993 | Sosnowski et al. |
| 5,250,033 | A | 10/1993 | Evans et al. |
| 5,275,611 | A | 1/1994 | Behl |
| 5,279,554 | A | 1/1994 | Turley |
| 5,290,276 | A | 3/1994 | Sewell, Jr. |
| 5,304,119 | A | 4/1994 | Balaban et al. |
| 5,312,360 | A | 5/1994 | Behl |
| 5,316,360 | A | 5/1994 | Feikema |
| 5,320,611 | A | 6/1994 | Bonutti et al. |
| 5,383,859 | A | 1/1995 | Sewell, Jr. |
| 5,392,766 | A | 2/1995 | Masterson et al. |
| 5,403,278 | A | 4/1995 | Ernst et al. |
| 5,407,430 | A | 4/1995 | Peters |
| 5,431,655 | A | 7/1995 | Melker et al. |
| 5,431,676 | A | 7/1995 | Dubrul et al. |
| 5,433,708 | A | 7/1995 | Nichols et al. |
| 5,437,631 | A | 8/1995 | Janzen |
| 5,437,644 | A | 8/1995 | Nobles |
| 5,453,094 | A | 9/1995 | Metcalf et al. |
| 5,454,790 | A | 10/1995 | Dubrul |
| 5,460,170 | A | 10/1995 | Hammerslag |
| 5,484,403 | A | 1/1996 | Yoakum et al. |
| 5,487,739 | A | 1/1996 | Aebischer et al. |
| 5,540,658 | A | 7/1996 | Evans et al. |
| 5,542,928 | A | 8/1996 | Evans et al. |
| 5,573,517 | A | 11/1996 | Bonutti et al. |
| 5,601,559 | A | 2/1997 | Melker et al. |
| 5,601,591 | A * | 2/1997 | Edwards et al. .............. 606/198 |
| 5,662,614 | A | 9/1997 | Edoga |
| 5,674,240 | A | 10/1997 | Bonutti et al. |
| 5,713,867 | A | 2/1998 | Morris |
| 5,735,867 | A | 4/1998 | Golser et al. |
| 5,746,720 | A | 5/1998 | Stouder, Jr. |
| 5,797,886 | A * | 8/1998 | Roth et al. .................... 604/264 |
| 5,800,390 | A | 9/1998 | Hayakawa et al. |
| 5,800,409 | A | 9/1998 | Bruce |
| 5,814,058 | A | 9/1998 | Carlson et al. |
| 5,824,002 | A | 10/1998 | Gentelia et al. |
| 5,827,227 | A * | 10/1998 | DeLago ........................ 604/104 |
| 5,827,319 | A * | 10/1998 | Carlson et al. ............... 606/191 |
| 5,836,913 | A | 11/1998 | Orth et al. |
| 5,873,854 | A | 2/1999 | Wolvek |
| 5,882,345 | A | 3/1999 | Yoon |
| 5,902,282 | A | 5/1999 | Balbierz |
| 5,944,691 | A | 8/1999 | Querns et al. |
| 5,957,902 | A | 9/1999 | Teves |
| 5,961,499 | A | 10/1999 | Bonutti et al. |
| 5,971,960 | A | 10/1999 | Flom et al. |
| 6,030,364 | A | 2/2000 | Durgin et al. |
| 6,063,060 | A | 5/2000 | Moenning |
| 6,077,248 | A | 6/2000 | Zumschlinge |
| 6,080,174 | A | 6/2000 | Dubrul et al. |
| 6,095,967 | A | 8/2000 | Black et al. |
| 6,146,400 | A | 11/2000 | Hahnen |
| 6,162,236 | A | 12/2000 | Osada |
| 6,197,014 | B1 | 3/2001 | Samson et al. |
| 6,210,376 | B1 | 4/2001 | Grayson |
| 6,245,052 | B1 | 6/2001 | Orth et al. |
| 6,283,950 | B1 | 9/2001 | Appling |
| 6,293,909 | B1 | 9/2001 | Chu et al. |
| 6,306,124 | B1 | 10/2001 | Jones et al. |
| 6,325,789 | B1 | 12/2001 | Janzen et al. |
| 6,325,812 | B1 | 12/2001 | Dubrul et al. |

FOREIGN PATENT DOCUMENTS

| | | |
|---|---|---|
| EP | 0385920 | 9/1990 |
| GB | 2199247 | 7/1988 |
| WO | WO 92/19312 | 11/1992 |
| WO | WO 94/20026 | 9/1994 |
| WO | WO 95/30374 | 11/1995 |
| WO | WO 98 19730 | 5/1998 |

OTHER PUBLICATIONS

Product Brochure Bluntport, Auto Suture Company, a division of United States Surgical Corporation (1992)(1 page).

Product Brochure Dexide Inc., Dexide, Inc. (1992) (1 page).

* cited by examiner

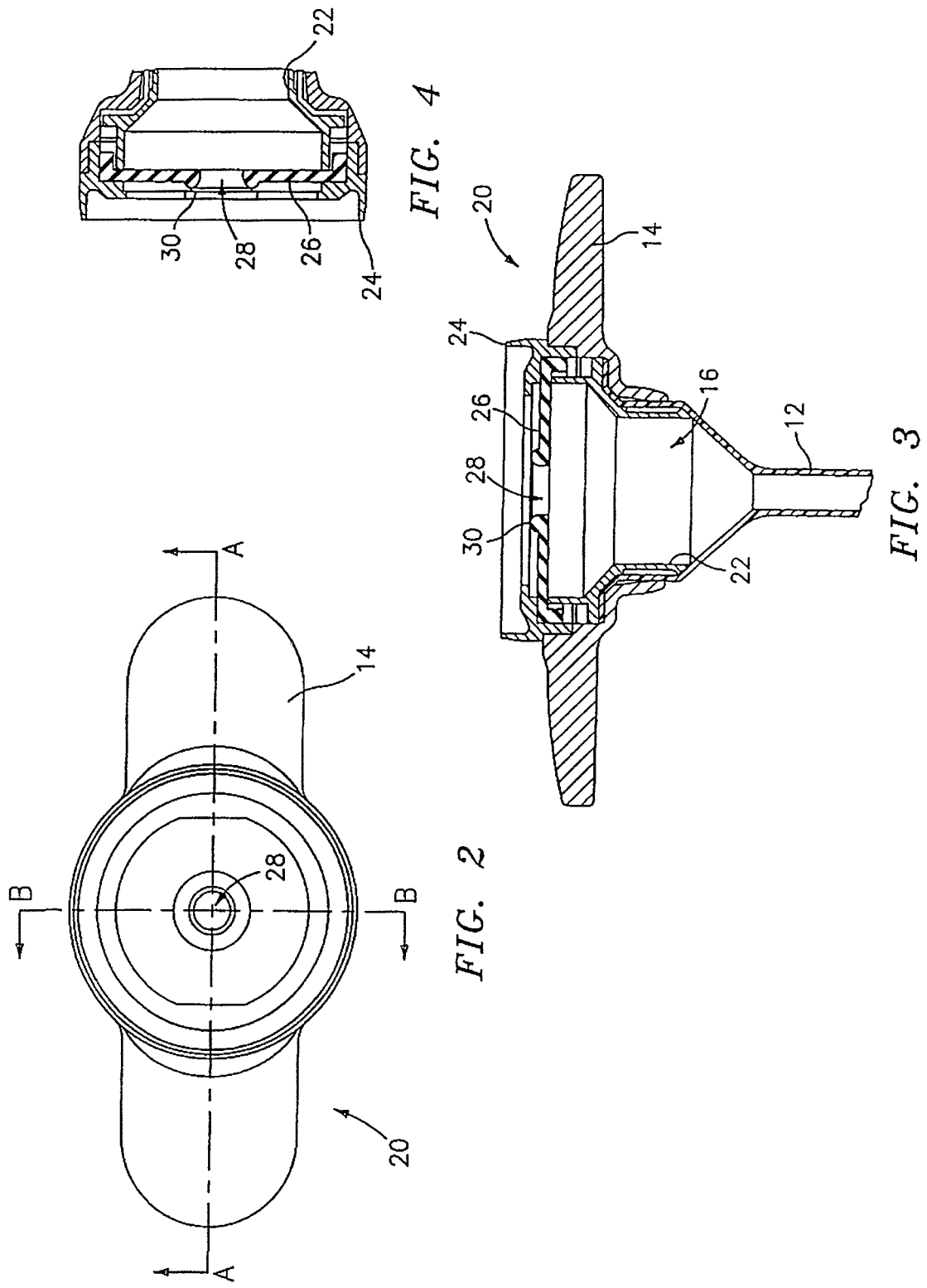

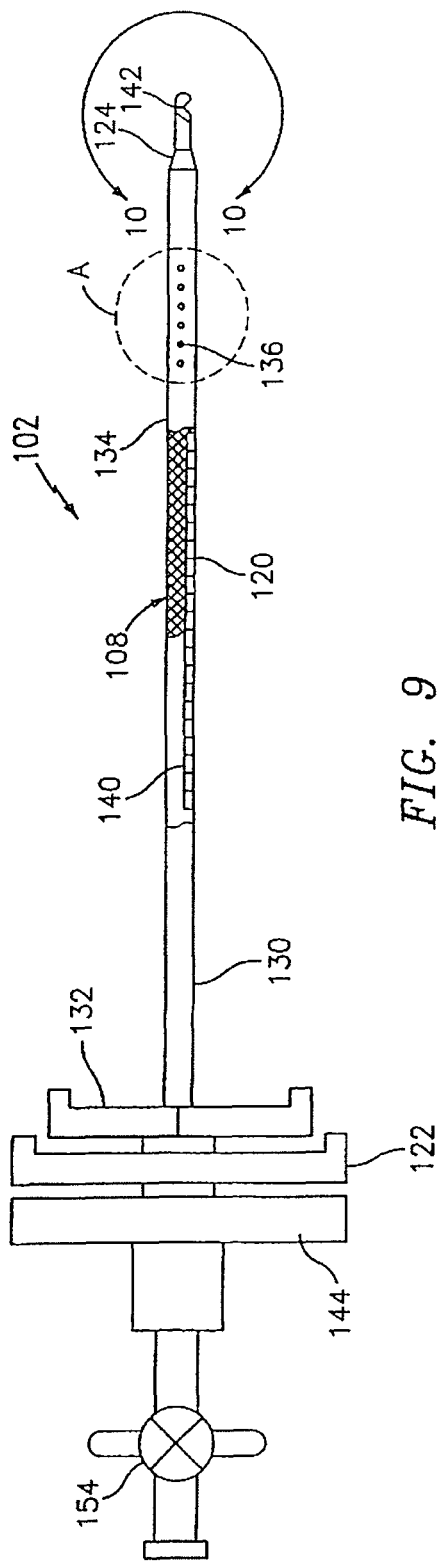
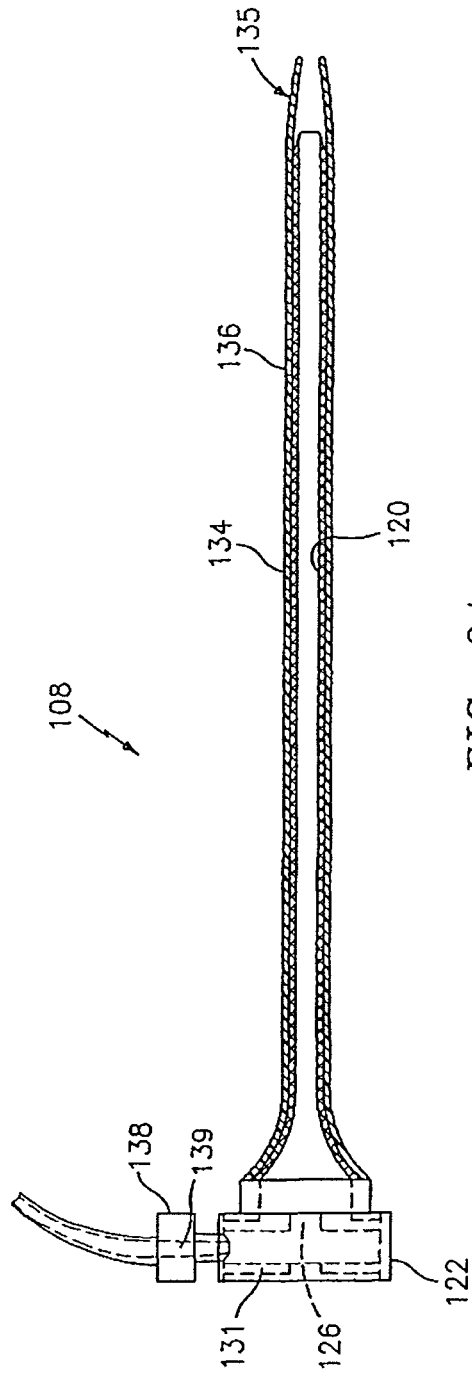
FIG. 9
FIG. 9A

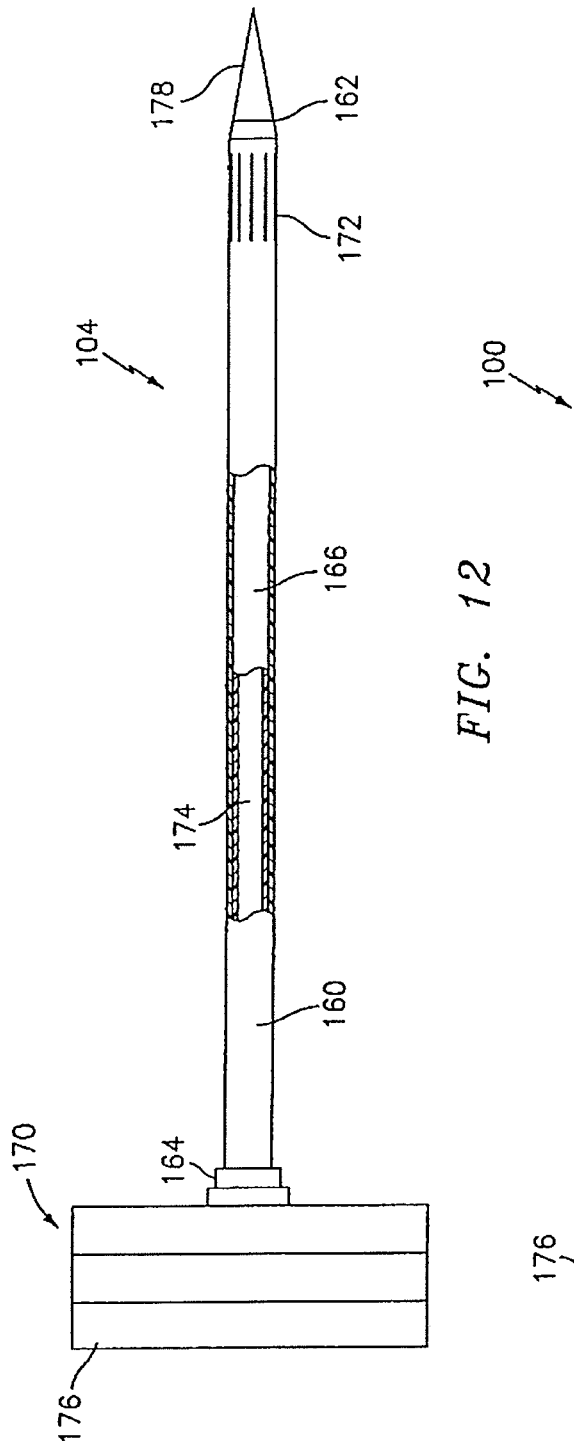
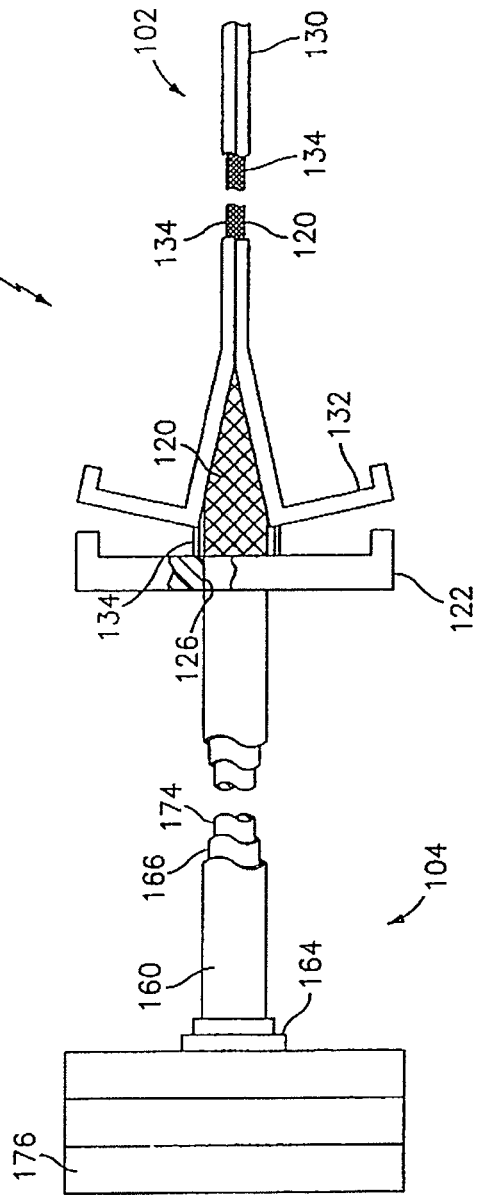
FIG. 12
FIG. 13

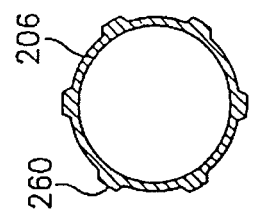
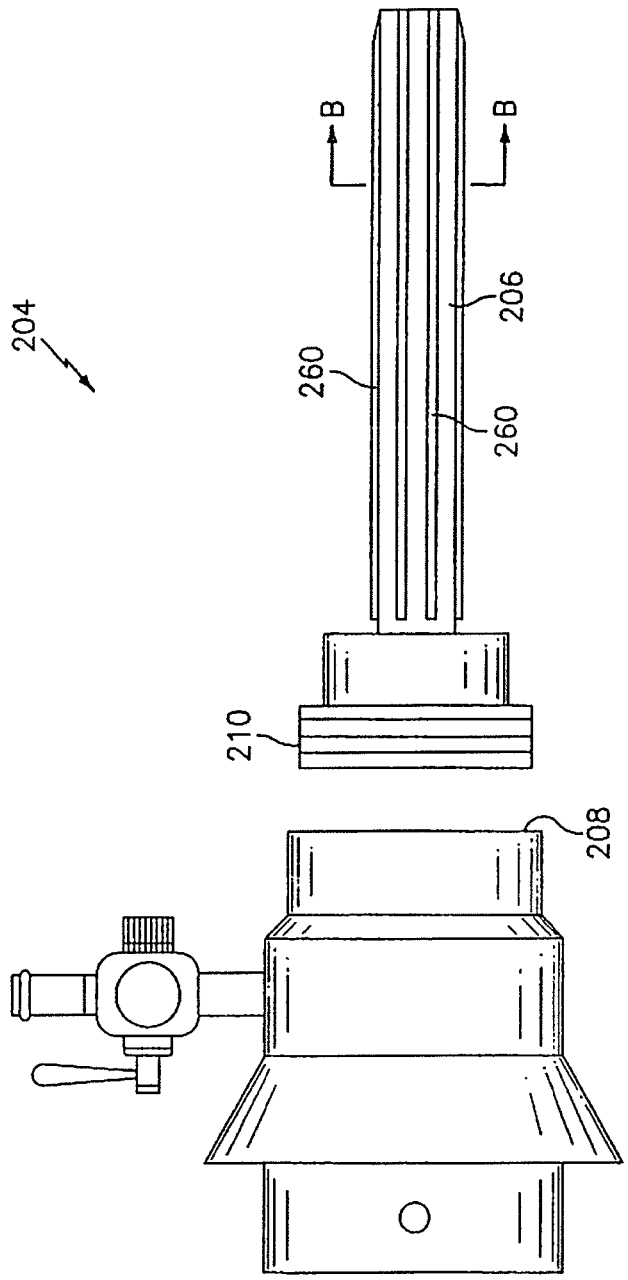
FIG. 24D
FIG. 24C

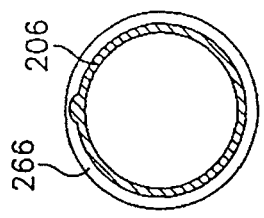
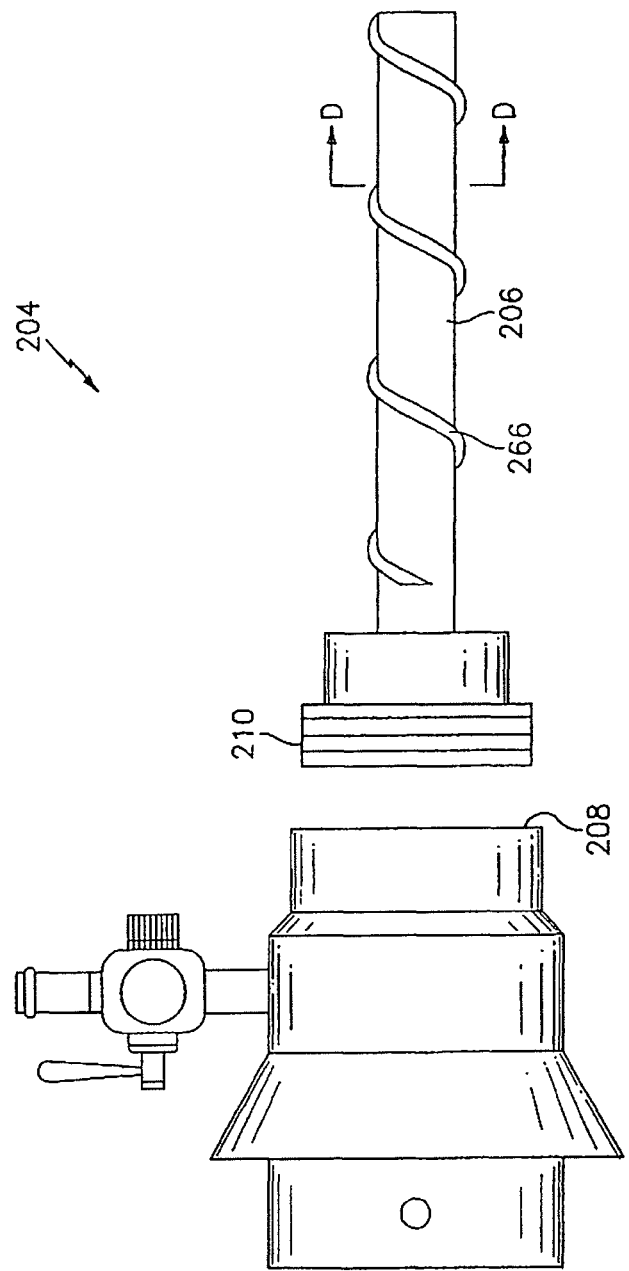
FIG. 24H
FIG. 24G

APPARATUS AND METHOD FOR PROVIDING PERCUTANEOUS ACCESS AND MEDICAMENT TO A TARGET SURGICAL SITE

CROSS-REFERENCE TO RELATED APPLICATION

The present application is a divisional of U.S. patent application Ser. No. 10/484,749 filed Jan. 21, 2004 now U.S. Pat. No. 7,449,011, which claims the benefit of and priority to International Application Serial No. PCT/US02/24308 filed on Jul. 31, 2002, which, in turn, claims the benefit of and priority to U.S. Provisional Patent Application Ser. No. 60/309,252 filed Aug. 1, 2001, the entire contents of each are hereby incorporated by reference.

BACKGROUND

1. Technical Field

The present disclosure relates generally to apparatus and methods for providing percutaneous access to an internal operative site during a surgical procedure and, more particularly, to apparatus and methods for creating a fluid-tight seal around an outer surface of a surgical instrument inserted therethrough, for reducing the amount of insertion force required to insert a surgical instrument therein and for delivering a medicament to the target delivery site.

2. Background of Related Art

Minimally invasive surgical procedures are performed throughout the body and generally rely on obtaining percutaneous access to an internal surgical site using small diameter tubes (typically 5 to 12 mm), usually referred to as trocars, which penetrate through the skin of the patient and open adjacent the desired surgical site. A viewing scope is introduced through one such trocar, and the surgeon operates using instruments introduced through other appropriately positioned trocars while viewing the operative site on a video monitor connected to the viewing scope. The surgeon is thus able to perform a wide variety of surgical procedures requiring only a few 5 to 12 mm punctures through the patient's skin, tissue, etc. adjacent the surgical site.

Certain minimally invasive surgical procedures are often named based on the type of viewing scope used to view the area of the body which is the operative site. For example, laparoscopic procedures use a laparoscope to view the operative site and are performed in the interior of the abdomen through a small incision. Such laparoscopic procedures typically require that a gas, such as carbon dioxide, be introduced into the abdominal cavity. This establishes pneumoperitoneum wherein the peritoneal cavity is sufficiently inflated for the insertion of trocars into the abdomen.

Pneumoperitoneum is established through the use of a special insufflation needle, called a Veress needle, which has a spring-loaded obturator that advances over the sharp tip of the needle as soon as the needle enters the abdominal cavity. This needle is inserted through the fascia and through the peritoneum. Generally, the surgeon relies on tactile senses to determine the proper placement of the needle by recognizing when the needle is inserted through the fascia and then through the peritoneum. After establishing pneumoperitoneum, the next step in laparoscopic surgery involves the insertion of a trocar, obturator or trocar/obturator assembly into the abdominal cavity.

Preferably, the trocars used in laparoscopic procedures should be readily sealable to inhibit the leakage of the insufflation gas from the abdominal cavity, in particular, should be designed to inhibit leakage from the region between the external periphery of the trocar and the abdominal wall.

In order to reduce the amount of insufflation gas which escapes from the abdominal cavity, a radially expandable access system has been developed to provide improved sealing about the periphery of the trocar. A system for performing such a function is commercially available from United States Surgical, a division of Tyco Healthcare, Ltd. under the trademark VERSAPORT™. Certain aspects of the expandable access system are described in commonly assigned U.S. Pat. Nos. 5,431,676; 5,814,058; 5,827,319; 6,080,174; 6,245,052 and 6,325,812, the entire contents of which are expressly incorporated herein by reference.

As disclosed therein, the expandable access system includes a sleeve having a sleeve body, typically made up of a radially expandable braid covered by an elastomeric layer. The braid initially has an inner diameter of about 2 mm and an outer diameter of about 3.5 mm. In use, passage of a surgical instrument (i.e., trocar, cannula, obturator, etc.) through the expandable access system causes radial expansion of the sleeve, typically to a final diameter of 5 mm, 10 mm or 12 mm. However, the sleeve can be expanded to any necessary diameter in order to accommodate the particular surgical instrument. The expandable access system further includes a handle affixed to a proximal end of the sleeve, the handle including a passage formed therein for the introduction of surgical instruments, through the handle, into the sleeve body.

A method of use of the expandable sealing apparatus includes inserting a pneumoperitoneum needle through the radially expandable sleeve body of the expandable access system to thereby form a needle/sleeve assembly. The needle/sleeve assembly is then introduced through the patient's abdomen by engaging the sharpened distal end of the pneumoperitoneum needle, protruding from the distal end of the sleeve body, against the body tissue of the body cavity and advancing the needle/sleeve assembly into the body cavity until the needle/sleeve assembly extends across the layers of the body tissue thereby forming an incision in the body tissue. The pneumoperitoneum needle is then removed from the body of the sleeve. A trocar, having a diameter smaller than the opening in the handle and larger than the lumen of the sleeve, is then introduced through the opening in the handle and into the abdomen of the patient. As a result, due to radial expansion of the sleeve by the trocar, the incision is subsequently also radially expanded. Trocars used in laparoscopic procedures include a valve at a proximal end thereof in order to permit passage of a viewing scope or other surgical instrument therethrough while simultaneously inhibiting escape of insufflation gas from the abdominal cavity.

Accordingly, in view of the need to maintain the atmospheric integrity of the abdominal cavity, a continuing need exists for a sealing assembly which reduces the escape of insufflation gas from the abdominal cavity and, more particularly from between the interface of the inner surface of the expandable access system and the outer surface of the surgical instrument (i.e., trocar).

In addition, a need exists for an access assembly which is capable of delivering a quantity of a medicament to a target surgical site. Still further, the need exists for an access system which requires a reduced insertion force for passing the cannula assembly through the expansion assembly.

SUMMARY

The present disclosure relates to a method of forming and enlarging a percutaneous penetration. The method includes the steps of providing a radially expandable dilation assembly having a needle assembly removably inserted in an axial lumen thereof, penetrating the dilation assembly and needle assembly through tissue to a target surgical site, withdrawing the needle assembly from the dilation assembly and inserting an expansion assembly into the axial lumen of the dilation assembly.

Preferably, the dilation assembly includes a tubular sleeve defining the axial lumen therethrough and a handle assembly operatively coupled to a proximal end of the tubular sleeve and defining an aperture formed therein, wherein the tubular sleeve is made up of a radially expandable tubular braid.

It is contemplated that the sleeve body includes a polymeric layer encasing the tubular braid. The polymeric layer preferably includes at least one radially oriented delivery hole formed near a distal end thereof.

Preferably, the dilation assembly includes a valve stem operatively coupled to the handle portion. The valve stem defines an injection lumen extending into the aperture formed in the handle portion.

It is contemplated that the handle portion of the radially expandable dilation assembly includes a seal extending across the aperture and disposed at a location proximal of the valve stem. The seal forms a fluid-tight seal around the expansion member upon insertion of the expansion member into the handle portion of the dilation assembly.

Preferably, the method further includes the step of injecting a fluid into the aperture of the handle portion after the expansion member is inserted into the dilation assembly. The seal prevents the fluid from escaping from the proximal end of the dilation assembly and in turn forces the fluid to flow distally through the dilation assembly.

It is contemplated that the expansion member includes at least one radially projecting element provided from the outer surface thereof. The at least one radially projecting element of the expansion member radially tents the sleeve body outward upon insertion of expansion member through the handle portion and into the sleeve body of the dilation assembly. The radially projecting element defines at least one channel extending along the length of the expansion member when the expansion member is inserted in the dilation assembly. Accordingly, the fluid flows along the at least one channel when the fluid is injected into the aperture of the handle portion.

It is contemplated that the dilation assembly includes at least one engaging member integrally formed with the handle portion and projecting radially inward. The expansion member includes at least one corresponding engaging element formed in an outer surface thereof for co-operable engagement with a respective engaging member of the dilation assembly. The at least one engaging member of the dilation assembly cooperates with the corresponding engaging element of the expansion member to axially advance the expansion member through the dilation assembly upon a rotation of the expansion member. Preferably, the engaging elements of the expansion assembly include at least one helical groove formed in an outer surface of the expansion member.

Preferably, the method further includes the steps of coupling the engaging member of the handle portion with the helical groove of the expansion member and rotating the expansion member relative to the dilation assembly in order to axially advance the expansion member through the dilation member. It is contemplated that the fluid can be injected through at least one of the engaging members into the corresponding helical groove such that the fluid flows out the distal end of the sleeve body via the helical groove.

These and other features of the assembly and method disclosed herein will become apparent through reference to the following description of embodiments, the accompanying drawings and the claims.

BRIEF DESCRIPTION OF THE DRAWINGS

The accompanying drawings, which are incorporated in and constitute a part of this specification, illustrate embodiments of the disclosure and, together with the general description given above, and the detailed description of the embodiments given below, serve to explain the principles of the present disclosure.

FIG. 2 is an enlarged end view of a handle assembly of the radially expandable dilation assembly of FIG. 1;

FIG. 3 is a side elevational view, in cross-section, of the handle assembly taken along line A-A;

FIG. 4 is a side elevational view, cross-section, of the handle assembly taken along line B-B;

FIG. 9 is a side view of a first component of a surgical access and medicament delivery system constructed in accordance with the principles of another aspect of the present disclosure;

FIG. 9A is a side cross-sectional view of the radially expandable sleeve of the first component of the surgical access and medicament delivery system of FIG. 9;

FIG. 12 illustrates an elongate expansion assembly constructed in accordance with the principles of the present disclosure, which forms a second component of the access and medicament delivery system;

FIG. 13 illustrates the use of the elongate expansion assembly of FIG. 12 for expanding the elongate dilation tube of FIG. 9 and splitting a sheath surrounding the braid of the radially expandable sleeve assembly;

FIG. 24C is a side elevational view of an expansion assembly constructed in accordance with another alternative embodiment of the present disclosure;

FIG. 24D is a distal end view of the expansion member depicted in FIG. 24C, taken along B-B;

FIG. 24G is a side elevational view of an expansion assembly constructed in accordance with another embodiment of the present disclosure;

FIG. 24H is a distal end view of the expansion member depicted in FIG. 24G, taken along D-D;

DETAILED DESCRIPTION OF PREFERRED EMBODIMENTS

Figure 1:
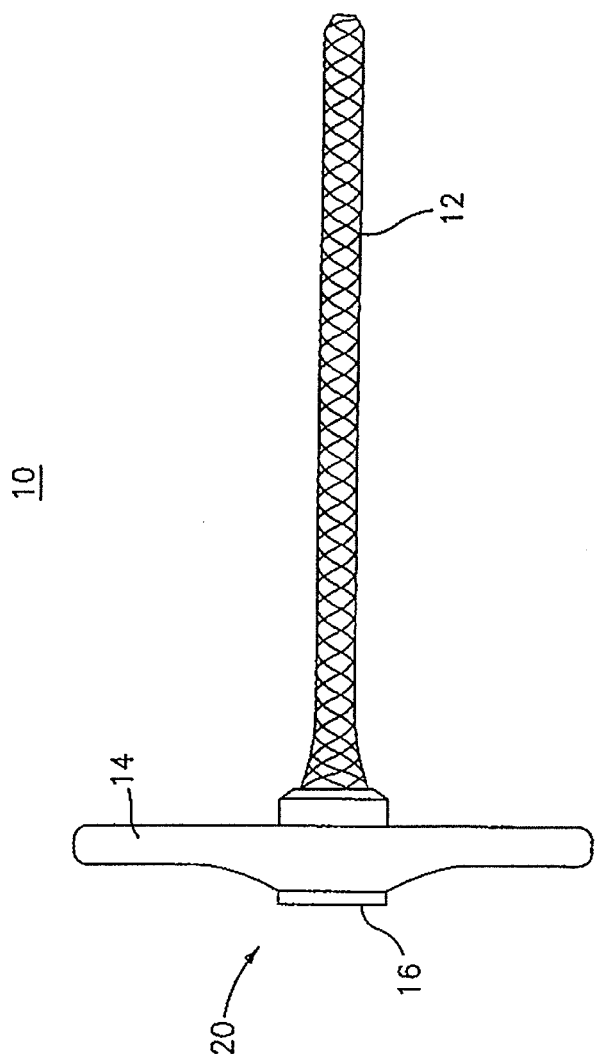
FIG. 1 is a side view of a radially expandable dilation assembly of an access system including an introducer seal in accordance with the present invention.

Preferred embodiments of the presently disclosed radially expandable dilation assembly of an access system will now be described in detail with reference to the drawing figures wherein like reference numerals identify similar or identical elements. In the drawings and in the description which follows, the term "proximal", as is traditional will refer to the end of the radially expandable sleeve of the present disclosure which is closest to the operator, while the term "distal" will refer to the end of the radially expandable dilation which is furthest from the operator.

Referring now in detail to the drawing figures in which like reference numerals identify similar or identical elements, a radially expandable dilation assembly of an access system is illustrated in FIGS. 1-4, and is generally designated 10. The presently disclosed radially expandable dilation assembly 10 contemplates the use of an introducer seal for the introduction of various types of surgical instruments through a handle assembly thereof, as will be described in greater detail below. Examples of such surgical instruments include, and are by no way limited to, trocars, cannulas, clip appliers, graspers, dissectors, retractors, staplers, laser fibers, photographic devices, endoscopes and laparoscopes, tubes and the like. Such instruments are collectively referred to herein as "surgical instruments".

Referring now to FIG. 1, radially expandable dilation assembly 10 includes a conformable sleeve body 12, defining a lumen therethrough, and a handle assembly 20 operatively coupled to a proximal end thereof. It is contemplated that sleeve body 12 includes a radially expandable braid covered by an elastomeric sleeve 134 (See FIGS. 9-22), made of, for example, polyurethane. Sleeve body 12 has an initial inner diameter of about 2 mm and an initial outer diameter of about 3.5 mm. In use, passage of a surgical instrument, in the form of a fixed radius expansion assembly, i.e., an obturator, into the lumen of sleeve body 12 causes radial expansion of sleeve body 12 from its initial diameter to a final diameter corresponding to the size of the surgical instrument received therein, typically about 5 mm, 10 mm or 12 mm. Radially expandable sleeve assembly 10 may be constructed in accordance with the details set forth in U.S. Pat. No. 5,431,676, the full disclosure of which is incorporated herein by reference.

Referring now to FIGS. 2-4, handle assembly 20 includes a handle portion 14, a lower housing part 22, and an upper housing part 24 which is preferably snap fit to lower housing part 22. Handle assembly 20 defines an aperture or passage 16 extending through upper housing part 24, handle portion 14 and lower housing part 22. Passage 16 provides access to the lumen of sleeve body 12. Handle assembly 20 further includes an introducer seal 26 clamped between lower and upper housing parts 22, 24 and extending across passage 16. Introducer seal 26 is provided with an opening 28 formed therein for providing access for an expansion assembly into passage 16 and subsequently into the lumen of sleeve body 12.

Introducer seal 26 is capable of accommodating surgical instruments of varying diameters, e.g., from about 5 mm to about 12 mm, while providing a fluid-tight seal about the outer surface of the surgical instrument, regardless of the particular diameter of the surgical instrument. In this manner, when a surgical instrument is inserted into the lumen of sleeve body 12, introducer seal 26 reduces the amount of insufflation gas escaping along the outer surface of the surgical instrument. Moreover, as will be described in greater detail below, introducer seal 26 reduces the amount of or prevents the escape of other fluids (i.e., medicament) from the proximal end of sleeve assembly 10.

Figure 5:
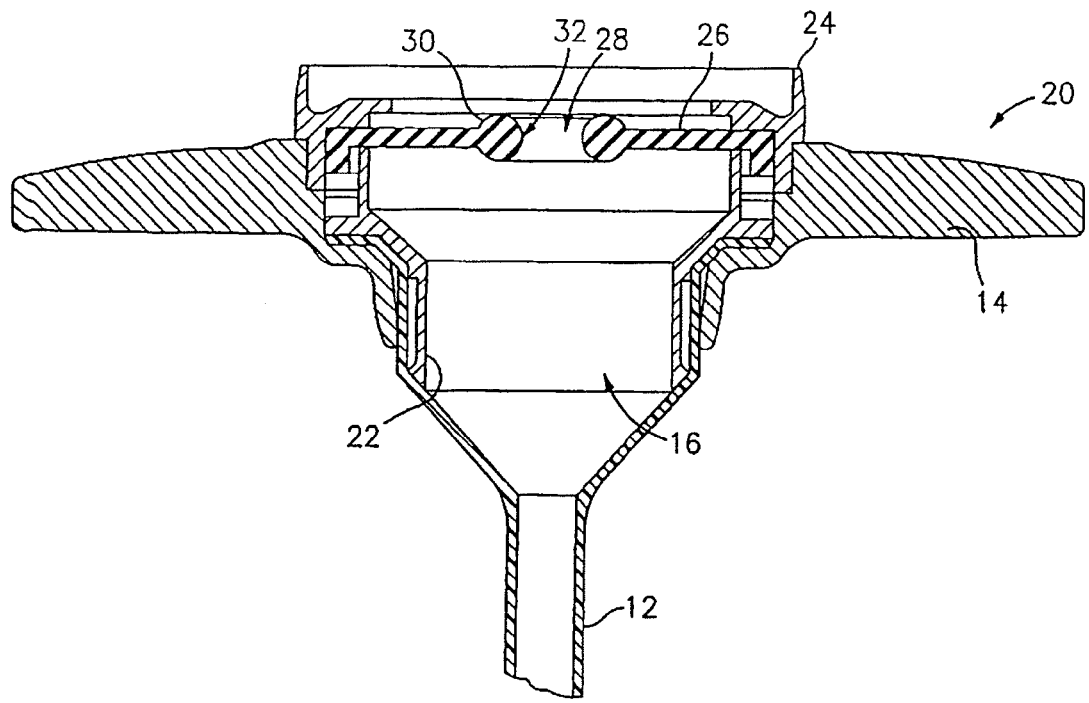
FIG. 5 is an enlarged side elevational view, in cross-section, of the handle assembly shown in FIG. 3 illustrating an alternative introducer seal in accordance with the present disclosure.

Preferably, introducer seal 26 includes an integrally formed raised rim portion 30 extending around a periphery of opening 28. Raised rim portion 30 provides opening 28 of introducer seal 26 with increased resiliency. As seen in FIGS. 3 and 4, rim portion 30 is provided on the proximal surface of introducer seal 26, however, it is envisioned that rim portion 30 can be provided on the distal surface of introducer seal 26 or on both the proximal and the distal surfaces of introducer seal 26. Turning now to FIG. 5, it is seen that introducer seal 26 may be provided with a toroidal rim 32 formed along the inner periphery of opening 28.

Figure 6:
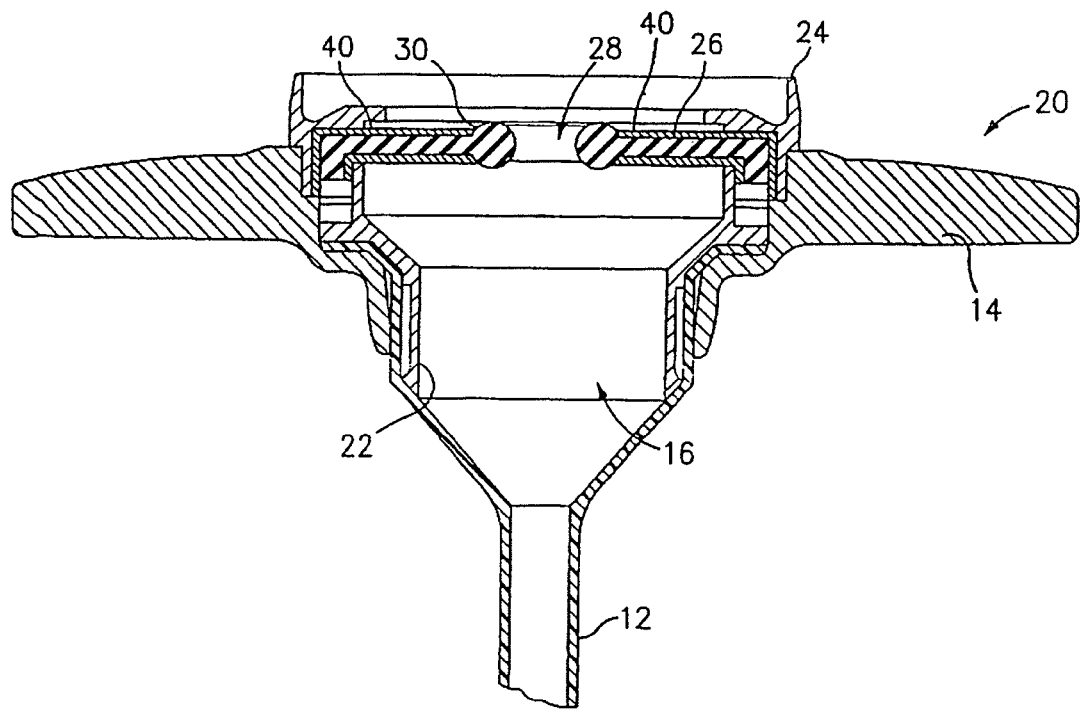
FIG. 6 is an enlarged side elevational view, in cross-section, of the handle assembly shown in FIG. 3 illustrating yet another introducer seal in accordance with the present disclosure.
Figure 7:
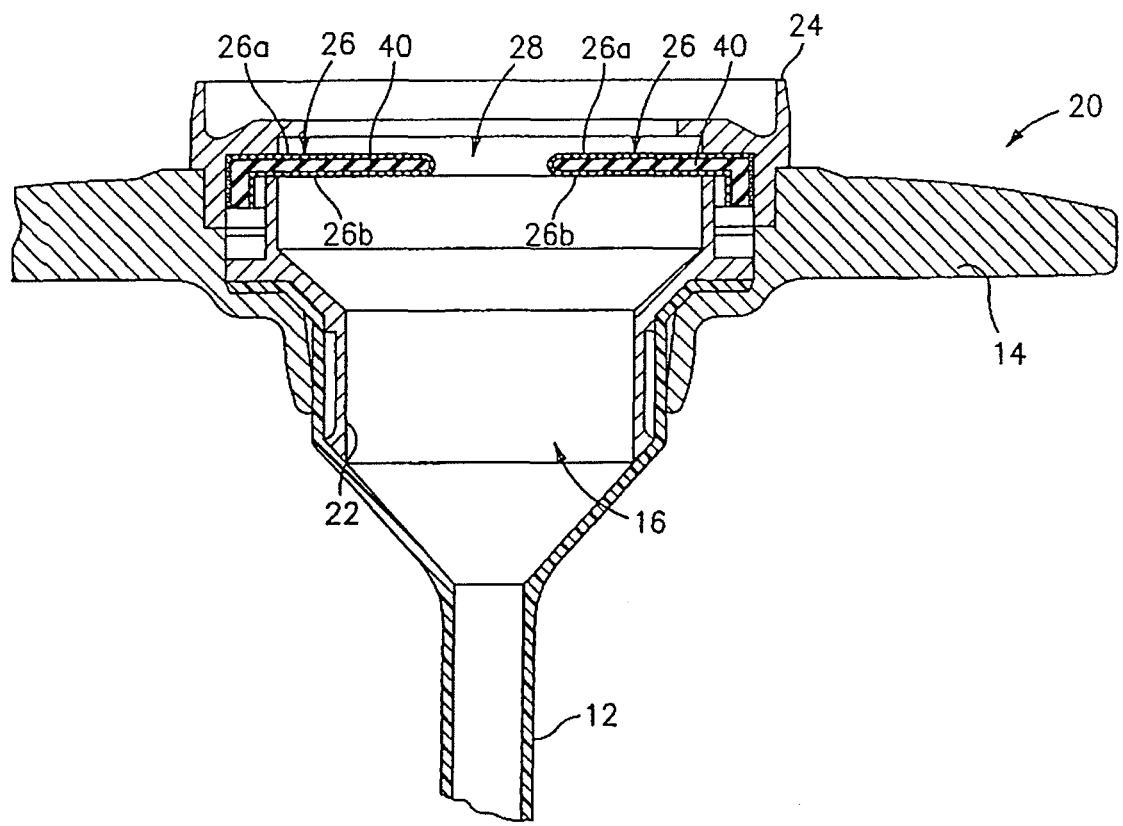
FIG. 7 is an enlarged side elevational view, in cross-section, of the handle assembly shown in FIG. 3, illustrating still another introducer seal in accordance with the present disclosure.

Preferably, introducer seal 26 is made from a resilient polymeric material, most preferably polyisoprene, or a combination of materials. As best seen in FIG. 6, introducer seal 26 may be provided with a layer of fabric 40 disposed on either the proximal surface, the distal surface or preferably on both the proximal and distal surfaces thereof. Fabric 40 may be any suitable fabric, for example, a spandex-like material (i.e., spandex is typically defined by having long chain synthetic polymers comprised of at least 85% by weight of segmented polyurethane) containing about 20% LYCRA and about 80% NYLON available from the Milliken & Company. As seen in FIG. 7, an alternative embodiment of introducer seal 26 is shown. In the embodiment of FIG. 7, introducer seal 26 includes a fabric layer 40 enveloped between upper and lower polyisoprene layers 26a and 26b, respectively.

By way of example, one method of forming introducer seal 26, having a layer of fabric 40 disposed on a surface thereof, involves compressing a quantity of polyisoprene into a flat sheet. A single layer of fabric 40 is placed on one side of the flat sheet of polyisoprene and then compressed into the uncured flat sheet by compressing in a calender for example. If it is desired to have fabric 40 disposed on both sides of introducer seal 26, this process is also accomplished on the other side of the polyisoprene sheet. The fabric polyisoprene composite is then die cut into circular slugs having an outer diameter and an inner diameter which defines opening 28. The slugs are then placed in a hot compression mold to cure the polyisoprene. This step also serves to extrude the outer portions of introducer seal 26 which extend outwardly from an inner section of introducer seal 26.

During the above-described process the bleed through of the polyisoprene material into and/or through the layers of fabric 40 is regulated by the density of the fabric selected. A greater degree of bleed-through of polyisoprene provides greater resistance to fraying of fabric 40 upon repeated insertion of instruments through introducer seal 26. However, too much bleed-through of the polyisoprene through fabric 40 will increase friction forces upon instruments being inserted through introducer seal 26.

In order to reduce friction between surgical instruments and introducer seal 26, as surgical instruments are inserted through handle assembly 20, a substance such as a lubricant may be applied to introducer seal 26 or, in the alternative, to the surgical instrument. A particularly effective lubricant is a hydrocyclosiloxane membrane prepared by a plasma polymerization process. Such a lubricant is available from Innerdyne, Inc. of Salt Lake City, Utah, U.S.A., and is disclosed in U.S. Pat. No. 5,463,010 which issued to Hu et al. on Oct. 31, 1995, the entire contents of which are hereby incorporated by reference.

Figure 8:
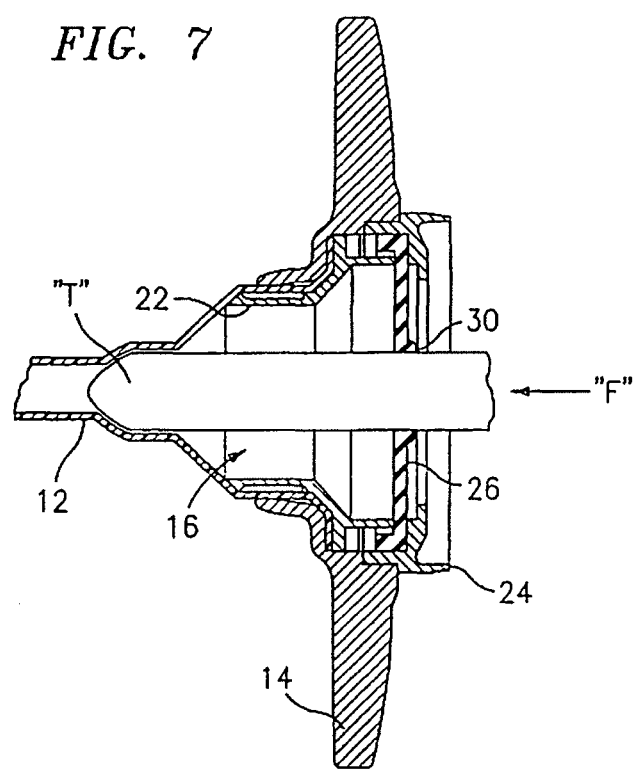
FIG. 8 is a side elevational view, in cross-section, of the handle assembly shown in FIG. 3, illustrating the insertion of a surgical instrument therethrough.

Insertion of a surgical instrument, such as a trocar "T", through opening 28 of introducer seal 26 and distally, in a direction of arrow "F", into the lumen of sleeve body 12, is shown in FIG. 8. With radially expandable dilation sleeve assembly 10 inserted through a percutaneous incision, as trocar "T" is inserted through opening 28 of introducer seal 26, trocar "T" stretches opening 28 radially outward thereby creating a fluid-tight seal between the outer surface of trocar "T" and introducer seal 26. As trocar "T" is further distally advanced through handle assembly 20 of radially expandable dilation assembly 10, trocar "T" enters the lumen of sleeve body 12 thereby expanding sleeve body 12 radially outward as well as radially expanding an incision made in a body wall and effectively sealing the perimeter of the incision against the escape of insufflation gas. In other words, insufflation gas is prevented from escaping from between the incision in the body wall and sleeve body 12 due to the radial expansion of sleeve body 12 against the incision as well as prevented from escaping from within radially expandable sleeve body 12 due to the fluid-tight seal created about the outer surface of trocar "T" by rim portion 30 of introducer seal 26.

In accordance with another aspect of the present disclosure, an access and medicament delivery system is disclosed for forming and enlarging percutaneous penetrations into a variety of target locations within a patient's body for a multiplicity of purposes and to deliver a quantity of a medicament to the target surgical site. Additional purposes include drainage, intra-organ drug administration, feeding, perfusion, aspiration and the like, and introducing viewing scopes and surgical instruments for use in minimally invasive surgical procedures, endoscopic procedures and the like.

The access and medicament delivery system includes a number of individual components that can be assembled into different size configurations. The assembled components can also be disassembled after use, and the components selectively sterilized or replaced prior to reassembling the access system for further use with a different patient. The different components and component assemblies and subassemblies will be described in greater detail below.

Sterilization of the components of the access and medicament delivery system can be accomplished by any suitable conventional sterilization technique, including heat (e.g., steam and autoclaving), chemical treatment (e.g., ethylene oxide exposure, radiation, etc.) and the like. After use, reusable components will be washed to remove blood and other contaminating substances and then sterilized, preferably by exposure to steam. Disposable components will usually be radiation sterilized in their packages prior to distribution. Thus, disposable components are ready to use out of the package.

Referring now to FIGS. 9-22, and in particular initially to FIGS. 9-14, an exemplary access and medication delivery system will be described. The three principle components of the access and medicament delivery system are an elongate dilation assembly 102, best illustrated in FIGS. 9-11, one or more elongate expansion assemblies 104, best illustrated in FIG. 12, and a valve member 106, best illustrated in FIG. 14.

Figure 10:
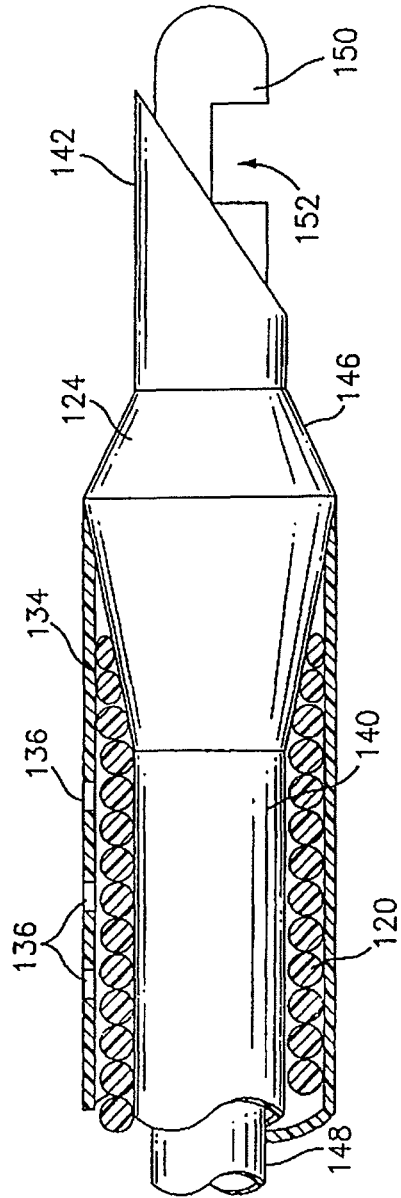
FIG. 10 is a detailed view, partly in cross-section taken at region 10-10 of the surgical access and medicament delivery system of FIG. 9.
Figure 11:
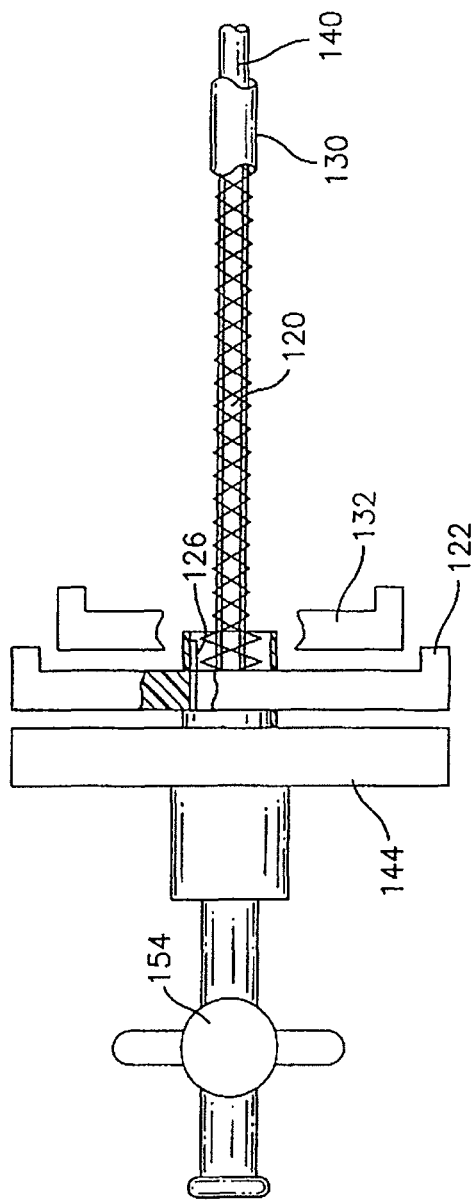
FIG. 11 is a detailed view of the proximal end of the surgical access and medicament delivery system of FIG. 9, shown with parts separated.

Elongate dilation assembly 102 includes an elongate dilation member 108 (similar in structure to radially expandable dilation assembly 10 described above) having a tubular braid 120 defining an axial lumen therethrough and a handle 122 connected to a proximal end of braid 120. Handle 122 has a passage 126 provided therein (see FIG. 9A) to permit passage of expansion assemblies 104 into the axial lumen of tubular braid 120. Tubular braid 120 is encased by a removable sheath 130 having a handle 132 at a proximal end thereof. Sheath 130 extends the entire length of tubular braid 120 and terminates at its distal end, generally at the location of a ferrule 124, as best illustrated in FIG. 10.

In a preferred embodiment, tubular braid 120 is laminated or covered with a coating, layer or sleeve 134 of elastic or plastically deformable material, such as silicone rubber, latex, polyethylene C-flex, or the like. Tubular braid 120 is percutaneously introduced while in its narrow-diameter configuration, and thereafter radially expanded using elongate expansion assemblies 104. Tubular braid 120 is preferably formed as a mesh of individual non-elastic filaments (e.g., composed of polyamide fiber (Kevlar®, DuPont), stainless steel, or the like) arranged such that radial expansion of braid 120 causes axial shortening of braid 120. Upon expansion, the braid filaments displace radially outwardly, thereby causing sleeve 134 to become pressed into the surrounding tissue and thereby anchoring dilation member 108 in place within the patient's tissue.

As best depicted in FIG. 9A, in conjunction with FIG. 9, sleeve 134 is provided with a plurality of radially oriented delivery holes 136 formed near a distal end thereof, as designated by region "A" in FIG. 9. In a preferred embodiment, delivery holes 136 are located along a single side of sleeve 134. Handle 122 of elongate dilation member 108 can be provided with a marking (not shown) on its outer surface, which marking is in linear alignment with delivery holes 136. In this manner, when tubular braid 120 is within the body cavity, the surgeon will be able to ascertain the orientation and direction of delivery holes 136 by observing the orientation and direction of the marking formed on handle 122. While delivery holes 136 have been disclosed above as being formed along a single side of sleeve 134, it is envisioned that diametrically opposed rows, multiple rows of radially oriented delivery holes or a plurality of randomly located delivery holes can be formed near a distal end of and around the periphery of sleeve 134. In another preferred embodiment, it is envisioned that delivery holes 136 can vary in diameter from a proximal portion of sleeve 134 toward a distal portion of sleeve 134.

In accordance with the present disclosure, as seen in FIG. 9A, elongate dilation member 108 is provided with a valve stem 138 operatively coupled to handle 122. Valve stem 138 is provided with a lumen 139 extending therethrough and opening into passage 126 of handle 122. As will be described in greater detail below, in use, valve stem 138 is coupled to a source of medicament (not shown) for the injection of a medicament "M", into passage 126 of handle 122, and ultimately on through tubular braid 120.

It is contemplated that handle 122 of elongate dilation member 108 preferably includes an introducer seal 131 disposed across the proximal most opening of handle 122. Preferably, introducer seal 131 includes all of the features of introducer seal 26 described above with regard to FIGS. 1-8. Further, as seen in FIG. 9A, the distal portion of sleeve 134 extends beyond the distal most portion of tubular braid 120 and defines a distal sealing cuff 135. In this manner, when elongate expansion assembly 104 is introduced into dilation member 108, introducer seal 131 acts to create a fluid-tight seal about a proximal portion thereof while sealing cuff 135 acts to create a fluid-tight seal about a distal portion thereof.

The access and medicament delivery system 100 further includes a sheath 130. Sheath 130 is preferably composed of a lubricous material, such as a thin-walled flexible plastic, such as polyethylene, tetrafluoroethylene, fluorinated ethylenepropylene, and the like. Sheath 130 protects tubular braid 120 during initial insertion of dilation member 108, but is removed from about braid 120 after dilation member 108 is in place. Preferably, sheath 130 will be weakened along an axial line to facilitate a splitting of sheath 130 at some point during the procedure, as will be described below.

A needle assembly 140 having a sharpened distal tip 142 and a proximal handle 144 is initially received within the axial lumen of tubular braid 120. Ferrule 124 is disposed near sharpened distal tip 142 of needle 140 and includes a forward tapered surface 146 (FIG. 10) which facilitates penetration of elongate dilation assembly 102 through the patient's skin, fascial tissues, and organ walls. In particular, ferrule 124 acts as a transition from the narrow diameter distal tip of needle assembly 140 to the slightly larger diameter removable sheath 130. Tubular braid 120 is received within an annular lumen which is defined between the outer surface of needle assembly 140 and the inner surface of sheath 130. Ferrule 124 defines a maximum diameter which is greater than the inner diameter of sleeve 134. Thus, withdrawal of needle 140 should cause sheath 130 to split, as will be further discussed below.

Needle assembly 140 is preferably in the form of an insufflation needle having a protective element at its distal tip 142. As illustrated, the protective element is an obturator 148 having a blunt distal end 150 which is reciprocatably received in the axial lumen of needle assembly 140. Obturator 148 is spring-loaded so that blunt end 150 extends distally from sharpened distal tip 142 of needle assembly 140 in its shelf or "at rest" configuration. As distal tip 142 of needle assembly 140 is pressed firmly against the patient's skin or other tissue, however, blunt end 150 will be retracted back into needle assembly 140 so that sharpened tip 142 can penetrate. Usually, obturator 148 will be hollow and include a port 152 at its distal end. By providing a valve assembly 154 (see FIGS. 9 and 11) at is proximal end, the combination of needle assembly 140 and obturator 148 can be used to introduce or withdraw insufflation fluids, particularly being useful for performing the initial stages of insufflation. Insufflation needles which can be modified for use in the present disclosure are available from United States Surgical Corporation, Norwalk, Conn. (available under the tradename Auto Suture® Surgineedle®).

Referring now to FIG. 12, a first elongate expansion assembly 104 will be described in detail. Expansion assembly 104 includes a fixed-radius tubular element 160 having a distal end 162 and a proximal end 164. An inner coaxial rod 166 is disposed within the axial lumen of fixed-radius tubular element 160, and is secured to tubular element 160 only at distal end 172. A handle assembly 170 is located at the proximal end of first elongate expansion assembly 104.

The axial lumen of fixed-radius tubular element 160 has a cross-sectional area which is greater than that of tubular braid 120 while tubular braid 120 is in its non-radially expanded configuration. Accordingly, by introducing expansion assembly 104 through the lumen of dilation member 108 and causing braid 120 to radially expand, an enlarged access channel will be provided by the lumen of fixed-radius tubular element 160. To facilitate introduction of elongate expansion assembly 104 through the axial lumen of dilation member 108, an internal obturator or rod 174 having a handle 176 at its proximal end and a tapered conical surface 178 at its distal end is preferably provided and positioned in the lumen of tubular element 160. Tapered conical surface 178 extends distally from tubular element 160 and acts to radially expand tubular braid 120 as expansion assembly 104 is advanced. Obturator 174 can then be removed from tubular element 160 to leave the access lumen of tubular element 160 unobstructed.

The length of elongate dilation tubular element 160 will vary depending on the intended usage, but will generally be in the range of from about 10 cm to about 25 cm. The length of dilation tubular elements intended for laparoscopic procedures will generally be in the range of from about 10 cm to about 20 cm, typically being in the range from about 10 cm to 15 cm. It will be appreciated that the length of elongate expansion assembly 104 will generally be somewhat greater than that of elongate dilation assembly 102, thus permitting the radial expansion of the entire length of dilation member 108 of dilation assembly 102.

Figure 14:
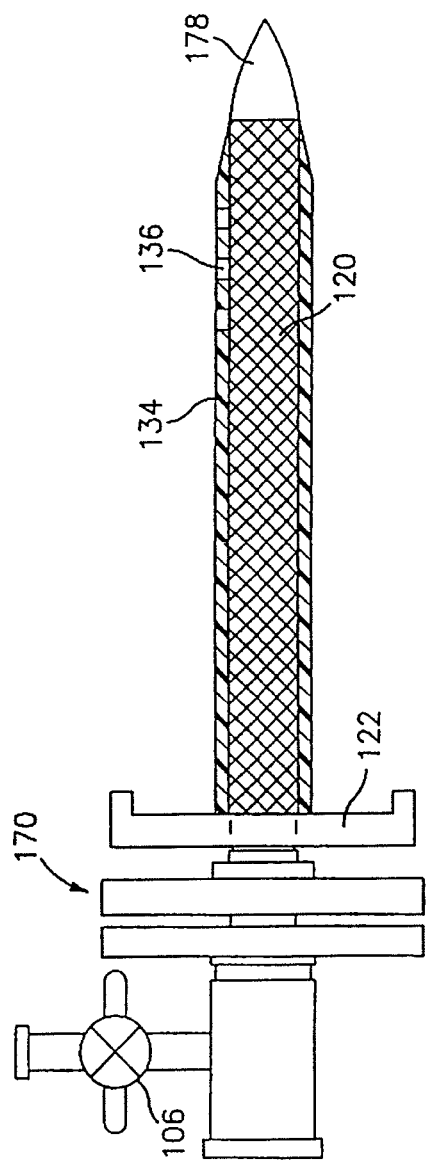
FIG. 14 illustrates the elongate dilation member of FIG. 9, shown after insertion of the elongate expansion assembly of FIG. 12 therein.

Referring now to FIGS. 13 and 14, insertion of elongate expansion assembly 104 through elongate dilation assembly 102 will be described in greater detail. It shall be appreciated by those skilled in the art that, prior to introducing expansion assembly 104, needle assembly 140 will have been removed from the axial lumen of dilation member 108 of dilation assembly 102. The tapered distal end 178 of obturator 174, positioned within elongate expansion assembly 104, is introduced through passage 126 in handle 122 and thus enters the axial lumen of dilation member 108. Sheath 130 will optionally have already been split by withdrawal of needle assembly 140 and passage of ferrule 124 through sheath 130. Alternatively, if needle assembly 140 does not cause sheath 130 to split, introduction of expansion assembly 104 through dilation assembly 102 will cause sheath 130 to split as a result of radial expansion of tubular braid 120 and sleeve 134. Eventually, introduction of expansion assembly 104 will result in the full expansion of braid 120, as illustrated in FIG. 14.

Figure 15:
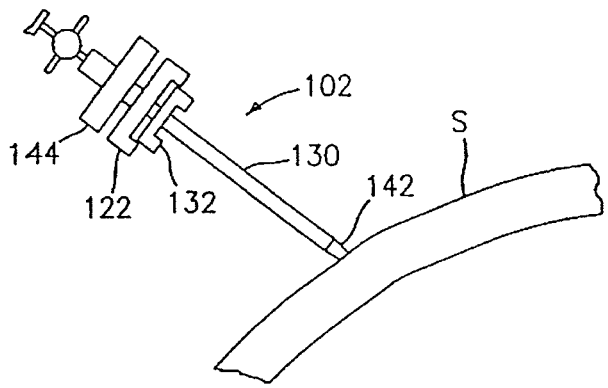
FIGS. 15-19 illustrate use of the surgical access and medicament delivery system of the present disclosure for forming and enlarging a percutaneous penetration.
Figure 16:
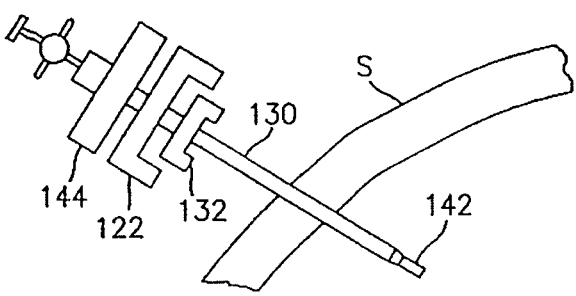

Referring now to FIGS. 15-22, use of the exemplary access and medicament delivery system of the present disclosure, for performing a percutaneous penetration and for delivering a medicament to a target surgical site will be described. Elongate dilation assembly 102 is initially positioned at a location on the patient's skin "S" where it is desired to form the penetration. Dilation assembly 102 is then penetrated through skin "S" by advancing sharpened distal tip 142 of needle assembly 140 (see FIG. 9) through skin "S" as illustrated in FIG. 15. In the case of laparoscopic procedures, as soon as sharpened tip 142 of needle assembly 140 penetrates through skin "S" and into the surgical site, blunt end 150 of obturator 148 automatically extends to protect the patient's internal organs from accidental injury. At this point, the lumen of needle assembly 140 may be used for insufflation if desired.

Figure 17:
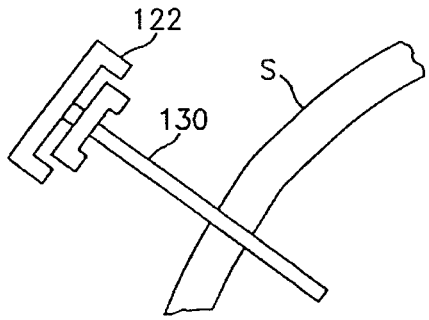
Figure 18:
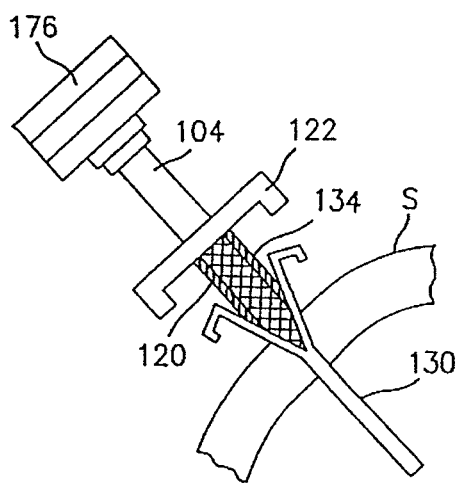
Figure 19:
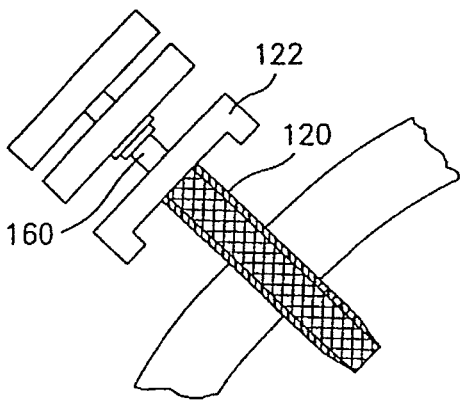

After dilation assembly 102 has been advanced to its desired location, needle assembly 140 will be withdrawn using handle 144, leaving sheath 130 (which may have been split by withdrawal of needle assembly 140 and attached ferrule 124) and tubular braid 120 with handle 122 at its proximal end therein, as illustrated in FIG. 17. Elongate expansion assembly 104 with mounted obturator 174 is next introduced through passage 126 of handle 122, thus expanding both tubular braid 120 and sleeve 134 and splitting sheath 130 (if not already split from above), as illustrated in FIG. 18. The presence of sleeve 134 and braid 120 facilitates radial expansion of the penetration which has been formed through skin "S". After expansion assembly 104 has been fully inserted through dilation assembly 102, obturator 174 will be removed from fixed radius tube 160, and sheath 130 will be withdrawn from over expanded tubular braid 120, as seen in FIG. 19. After expansion assembly 104 has been fully inserted through dilation assembly 102, inner coaxial rod 166 is removed from fixed-radius tube 160, and sheath 130 is removed from over expanded tubular braid 120.

Figure 20:
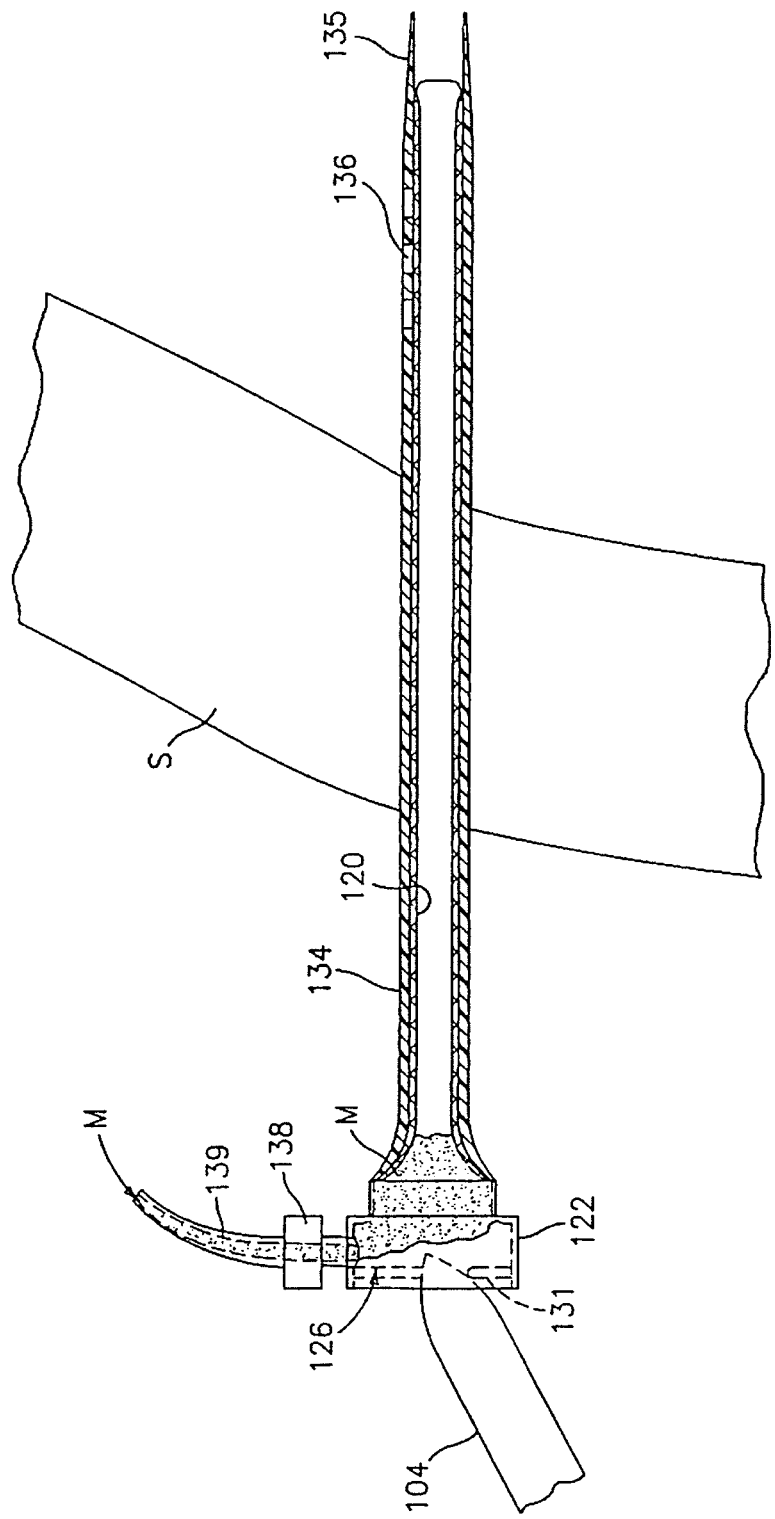
FIGS. 20-22 illustrate use of the surgical access and medicament delivery system of the present disclosure for delivering a medicament to a target surgical site.
Figure 21:
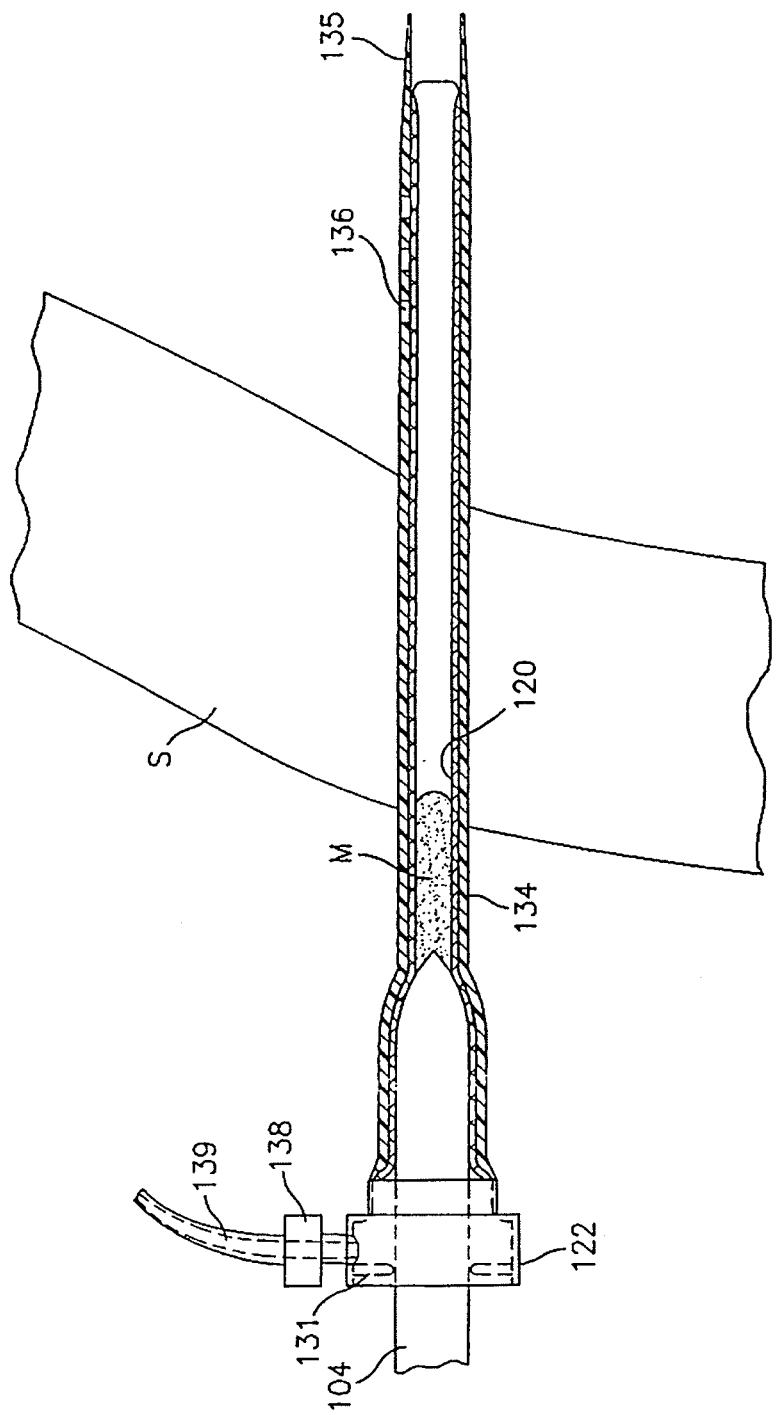
Figure 22:
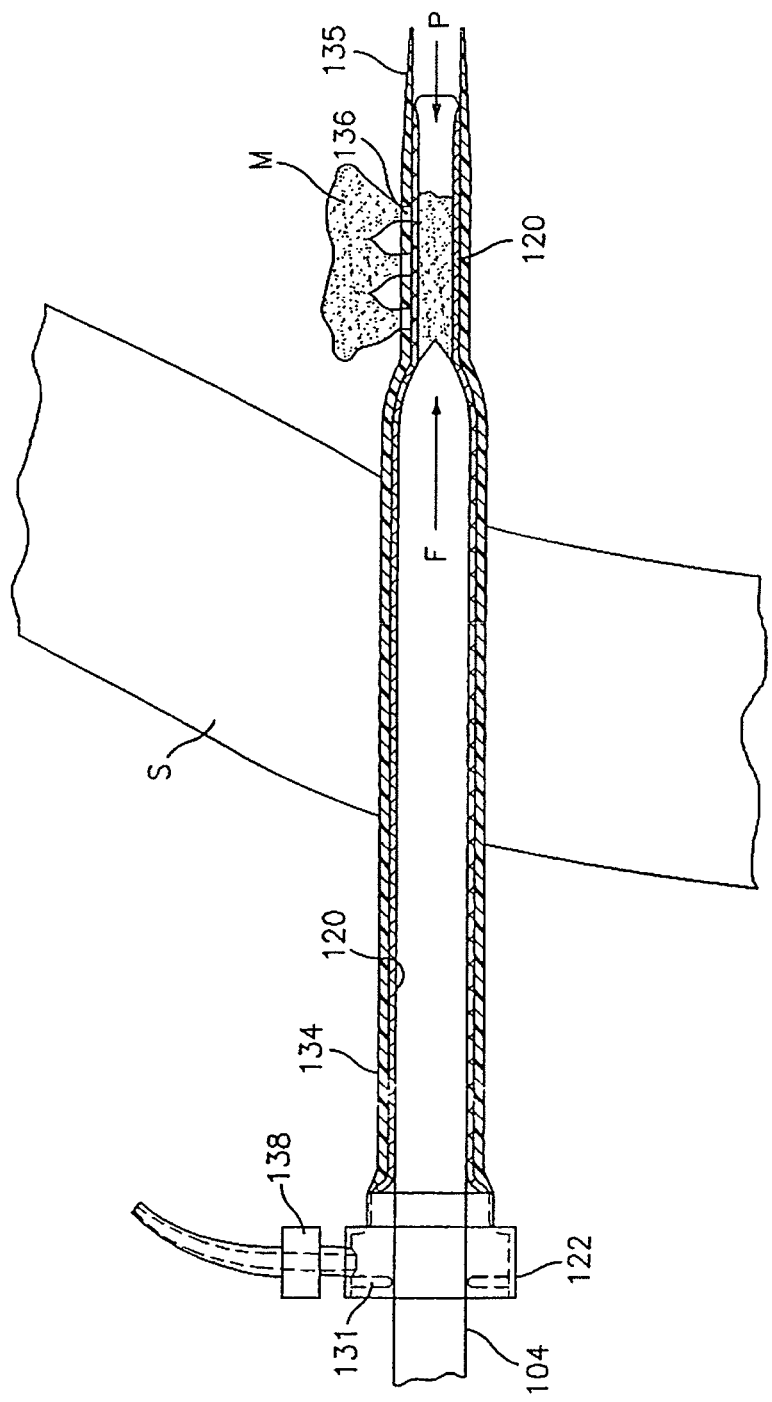

Referring now in particular to FIGS. 20-22, delivery of a medicament to the target surgical site, through the access and delivery system of the present disclosure, will be described in greater detail. After elongate dilation assembly 102 is in place, penetrating through skin "S" with the target surgical site insufflated with an appropriate gas and needle assembly 140 removed from dilation assembly 102, valve stem 138 is operatively and fluidly coupled to a source of medicament (not shown). As seen in FIG. 20, the surgeon then injects medicament "M", into passage 126 of handle 122 via lumen 139 of valve stem 138. With medicament "M" injected into passage 126 of handle 122 and the axial lumen of elongate dilation assembly 102, the distal end of elongate expansion assembly 104 is introduced into passage 126 of handle 122 through introducer seal 131 and advanced distally through tubular braid 120 and sleeve 134.

As seen in FIG. 21, distal advancement of expansion assembly 104 through sleeve 134 causes medicament "M" to be advanced distally through the axial lumen of tubular braid 120. In other words, expansion assembly 104 acts like a piston to drive medicament "M" distally through the axial lumen of tubular braid 120. Since tubular braid 120 is surrounded or encased by sleeve 134, medicament "M" is prevented from seeping radially outward through tubular braid 120. Further, introducer seal 131, which surrounds expansion assembly 104 and creates a fluid-tight seal around expansion assembly 104, prevents escape of medicament "M" from the proximal end of handle 122.

Turning now to FIG. 22, as expansion assembly 104 is further advanced distally, thereby further advancing medicament "M" through sleeve 134, medicament "M" will encounter delivery holes 136 formed near the distal end of sleeve 134. As medicament "M" passes across delivery holes 136 of sleeve 134, medicament "M" will be forced radially outward through delivery holes 136 and to the target surgical site due to an expansion member insertion force "F", acting in a distal direction on medicament "M", and an insufflation pressure "P", acting in a proximal direction on medicament "M". The opposing insertion force "F" and insufflation pressure "P" will cause medicament "M" to be dispensed radially outward through delivery holes 136 of sleeve 134.

Figure 23:
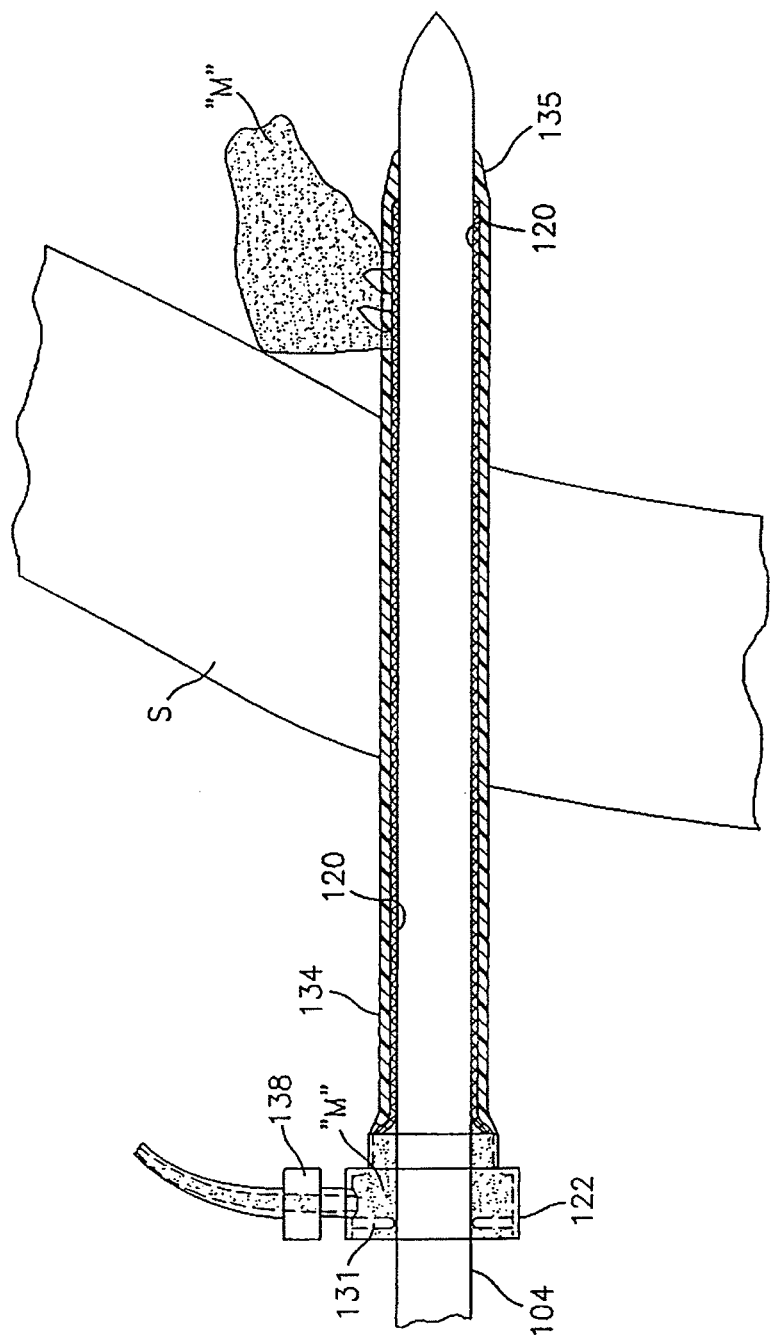
FIG. 23 illustrates an alternative method of delivering a medicament to a target surgical site using the surgical access and medicament delivery system of FIGS. 9-19.

Referring now to FIG. 23, an alternative method of use of the access and medicament delivery system of the present disclosure, for performing a percutaneous penetration and for delivering a medicament to a target surgical site will be described. With elongate dilation assembly 102 in place, penetrating through skin "S" and with the target surgical site insufflated and expansion assembly 104 fully received through tubular braid 120, valve stem 138 is operatively and fluidly coupled to a source of medicament (not shown). As seen in FIG. 23, introducer seal 131 creates a fluid-tight seal around a proximal portion of expansion assembly 104 while sealing cuff 135 creates a seal around a distal portion of expansion assembly 104.

According to the present embodiment, with expansion assembly 104 disposed within tubular braid 120 and sealed near its proximal and distal portions, the surgeon injects medicament "M" into passage 126 of handle 122 surrounding expansion assembly 104. Preferably, medicament "M" is a substantially non-viscous substance. Accordingly, since introducer seal 131 creates a barrier at the proximal portion of expansion assembly 104, injection of medicament "M" into passage 126 will result in a distal flow of medicament "M", between sleeve 134 of dilation assembly 102 and expansion assembly 104, along tubular braid 120. Tubular braid 120 acts like a manifold, providing medicament "M" with a capillary of passages through which it can flow. Since cuff seal 135 surrounds expansion assembly 104 and creates a fluid-tight seal therearound, when medicament "M" approaches the distal portion of tubular braid 120, medicament "M" is forced radially outward through delivery holes 136 to the target surgical site.

While delivery holes 136 have only been shown on a single side of sleeve 134, as disclosed above, delivery holes 136 can be formed around the entire periphery of sleeve 134 in order to deliver medicament "M" in all directions in the target surgical site. It is further contemplated that is no delivery holes 136 are formed in sleeves 134 and if cuff seal 135 is not provided at the distal end of sleeves 34, 134, that medicament "M" will be ejected from the distal end of tubular braid 120.

Turning now to FIGS. 24-29, an expansion assembly constructed in accordance with an alternative embodiment of the present disclosure, is generally designated 204. Expansion assembly 204 includes an expansion member (i.e., cannula) 206 and a proximal hub 208. Expansion member 206 includes a threaded connector 210 at its proximal end which can be removably secured to a fitting (not shown) in the distal end of proximal hub 208. Expansion member 206 defines a second cross-sectional area which is larger than the first cross-sectional area of sleeve body 12 and tubular braid 120.

Figures 24A, 24B:
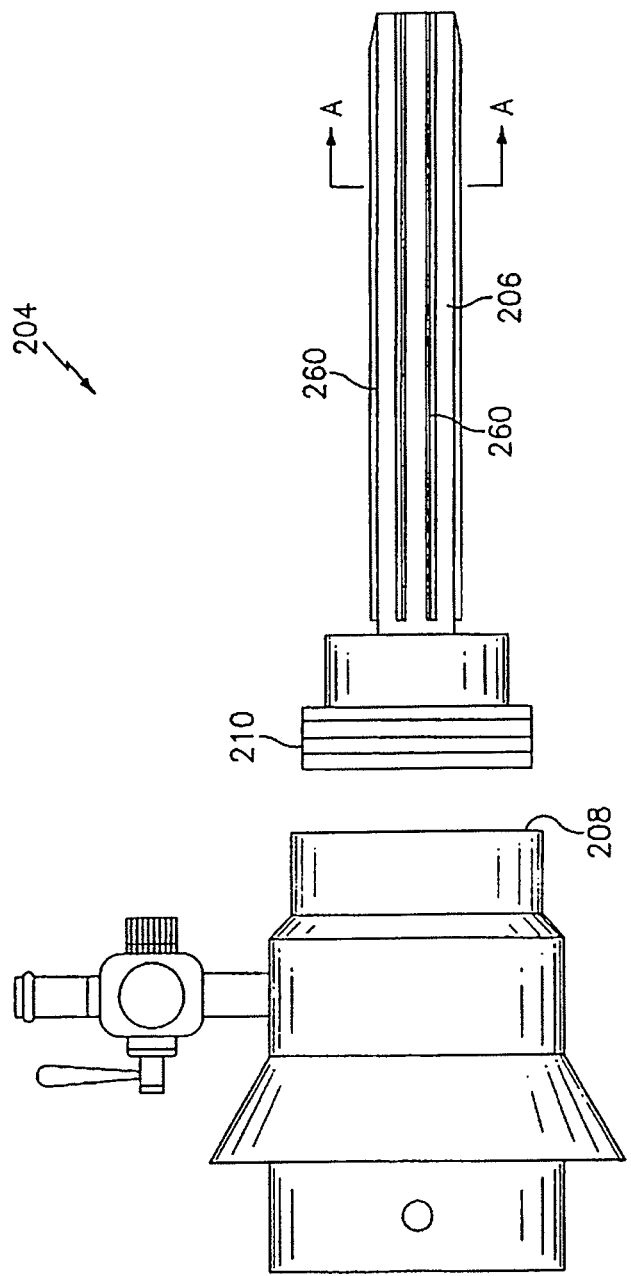
FIG. 24A is a side elevational view of an elongated expansion assembly, partially separated, illustrating an elongate expansion assembly constructed in accordance with an alternative embodiment of the present disclosure.
FIG. 24B is a distal end view of the expansion member depicted in FIG. 24A, taken along A-A.

In accordance with a preferred embodiment of the present disclosure, as seen in FIGS. 24A and 24B, expansion member 206 of expansion assembly 204 is provided with a plurality of longitudinally running raised ribs 260 formed along the outer surface thereof. As seen in particular in FIG. 24B, ribs 260 have a substantially triangular cross-sectional profile. As seen in particular in FIG. 24D, ribs 260 can have a substantially arcuate or semi-circular cross-sectional profile. Ribs 260 are preferably formed around the entire periphery of expansion member 206 and are evenly spaced from one another, as will be discussed in greater detail below.

Preferably, as seen in FIGS. 24B and 24D, six longitudinal ribs 260 are formed along the outer periphery of expansion member 206. While it is preferred that ribs 260 are evenly spaced from one another, it is contemplated that ribs 260 can be spaced any radial distance from one another. Preferably, a distal end of each rib 260 is tapered in height so as to facilitate the insertion of expansion assembly 204 into a proximal end of the lumen defined by sleeve body 12.

Figures 24E, 24F:
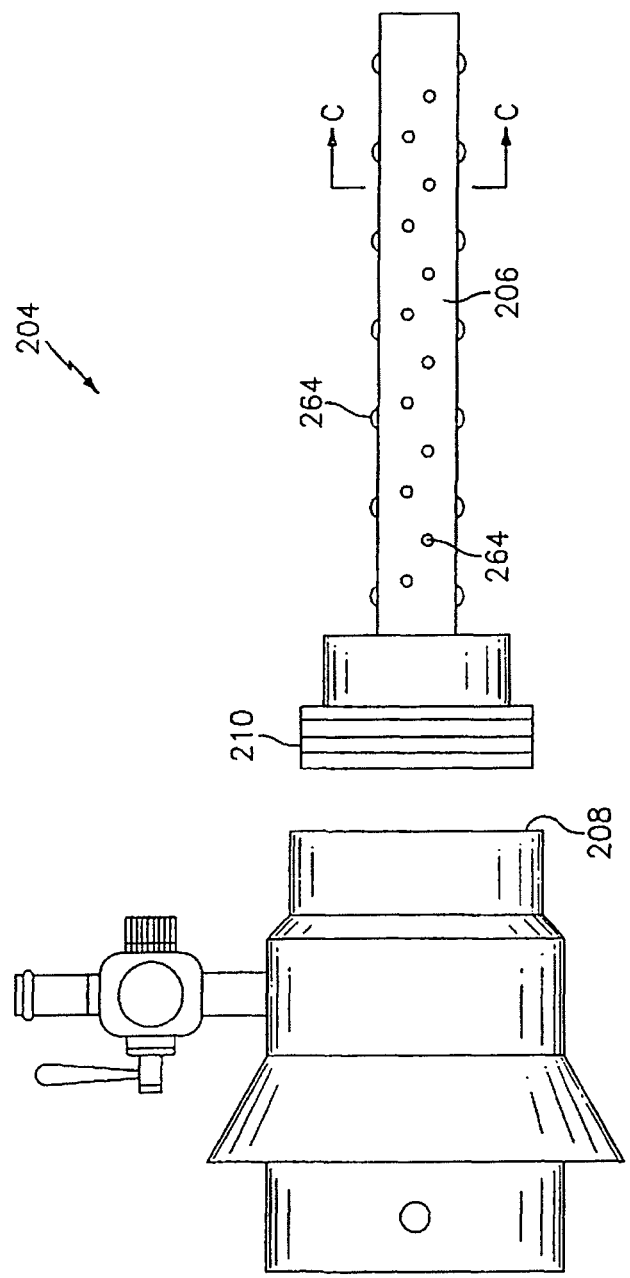
FIG. 24E is a side elevational view of an expansion assembly constructed in accordance with yet another embodiment of the present disclosure.
FIG. 24F is a distal end view of the expansion member depicted in FIG. 24E, taken along C-C.

As seen in FIGS. 24E and 24F, in an alternative embodiment, expansion member 206 of expansion assembly 204 can be provided with a plurality of raised bumps 264 formed along the entire outer surface thereof. It is envisioned that bumps 264 can be hemi-spherical, conical, pyramidal or the like. Turning now to FIGS. 24G and 24H, in yet another alternative embodiment, expansion member 206 is provided with a helical thread 266 formed on the outer surface thereof. Preferably, helical thread 266 extends from proximal hub 208 of expansion assembly 204 to the distal end of expansion member 206, however, it is envisioned that helical thread 266 can extend any distance along the length of expansion member 206.

Figure 24I:
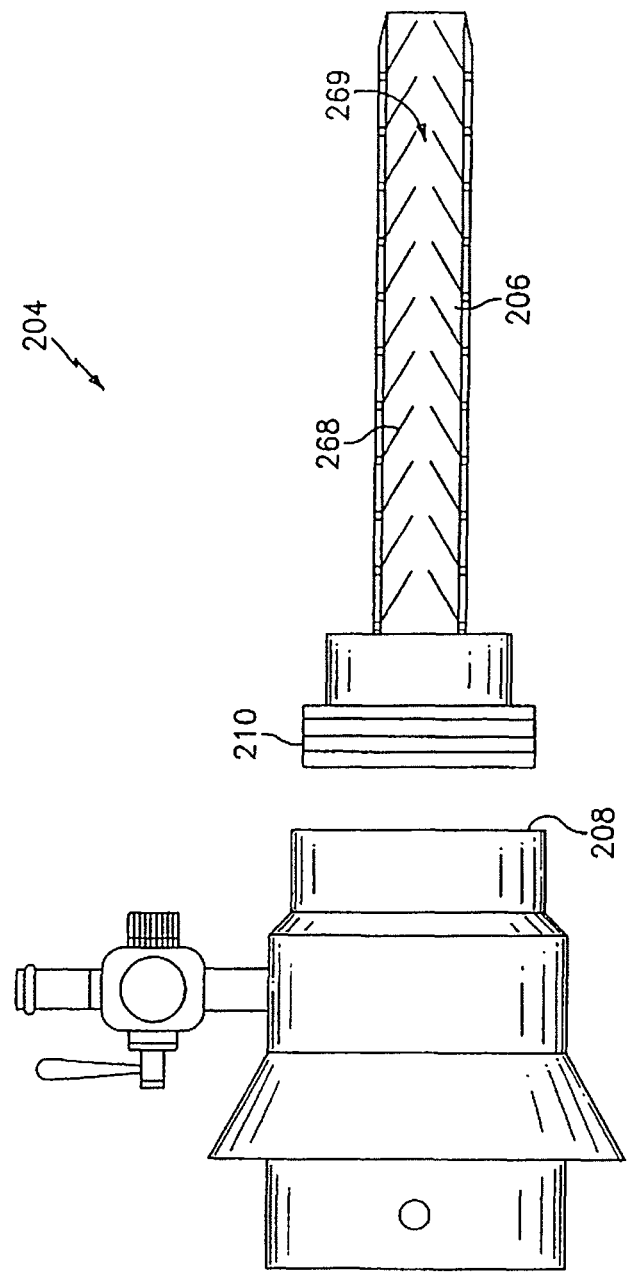
FIG. 24I is a side elevational view of an expansion assembly constructed in accordance with another embodiment of the present disclosure.

Turning now to FIG. 24I, in an alternative embodiment, expansion member 206 is provided with a series of diagonally oriented ribs 268 formed along the outer surface thereof, which ribs 268 define a generally V-shaped or tread like arrangement. Ribs 268 further define a plurality of channels 269 along the length of expansion member 206.

As will be described in greater detail below, ribs 260, 268, bumps 264 and helical thread 266 function to maintain an inner surface of sleeve body 12 spaced a radial distance away from expansion member 206 to thereby reduce the amount of surface area in contact between the inner surface of sleeve body 12 and the outer surface of expansion member 206 and to reduce the amount of frictional and resistive forces acting therebetween.

As described above, it is contemplated that dilation member 108 is provided with an introducer seal 131 and that dilation member 108 of dilation assembly 102 includes a valve stem 138 operatively coupled to handle 122 at a location distal of introducer seal 131.

Figure 25:
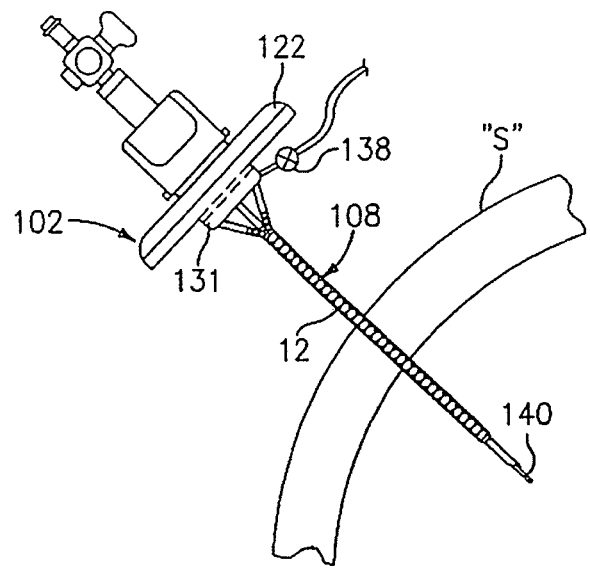
FIGS. 25-28 illustrate use of the expansion assembly of FIGS. 24A-24B in accordance with the present disclosure for providing access and delivering medicament to the abdomen of a patient.

Referring now in detail to FIGS. 25-28, use of the access and medicament delivery system according to the present embodiment of the disclosure will now be described. As seen in FIG. 25, elongate dilation assembly 102, having pneumoperitoneum needle assembly 140 inserted therein, is shown penetrating through the patient's skin "S" and extending across the layers of tissue. Introduction of elongate dilation assembly 102 is accomplished as described above with reference to FIGS. 15-19.

Figure 26:
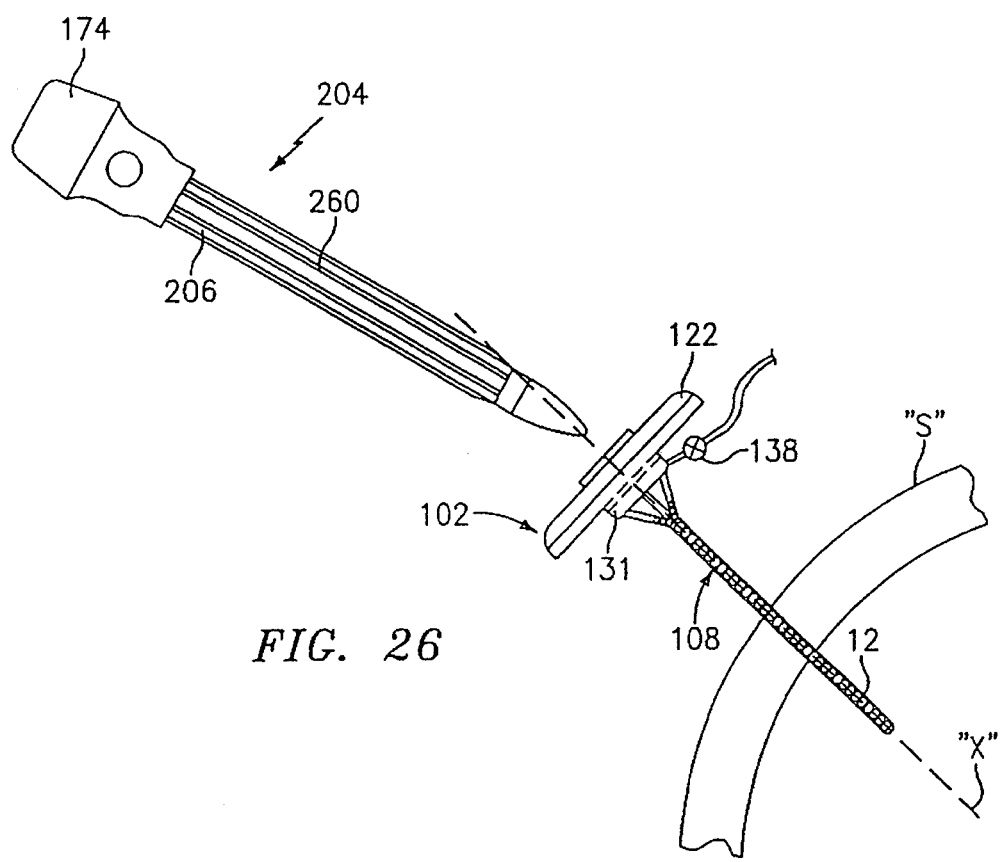
Figure 27:
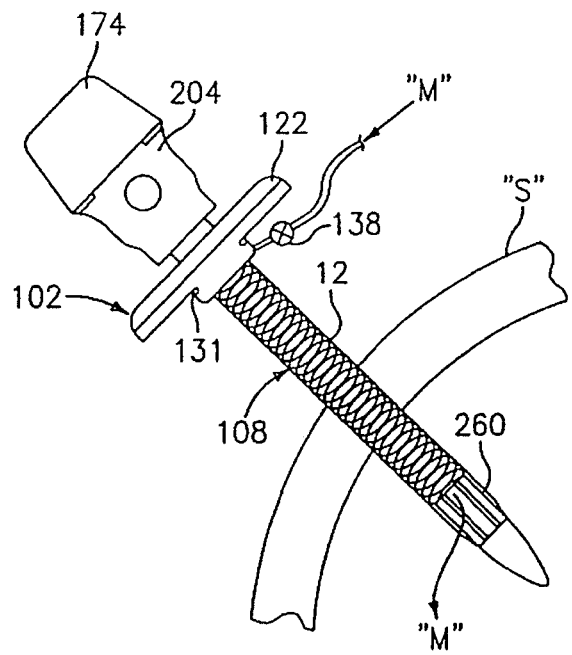
Figure 28:
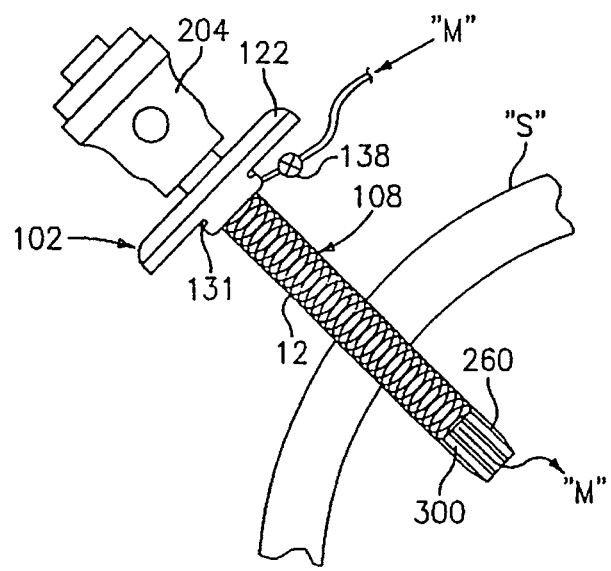

Needle assembly 140 is then removed, and expansion assembly 204 including an expansion member 206 and obturator 174 is introduced, as seen in FIG. 26, through introducer seal 131 and sleeve body 12 of dilation assembly 102, resulting in the radial expansion of sleeve body 12 of dilation member 108, as illustrated in FIG. 27. Accordingly, introducer seal 131 acts to form a fluid-tight seal around a proximal portion of expansion member 206. With expansion member 206 in place within sleeve body 12 of dilation member 108, obturator 174 can be removed from expansion member 206, as seen in FIG. 28.

According to the present embodiment, as expansion assembly 204 is advanced distally through sleeve body 12 of dilation assembly 102, the inner surface of sleeve body 12 will substantially only contact the upper edges or tips of ribs 260, 268, bumps 264 and thread 266 of expansion member 206. Since the inner surface of sleeve body 12 only contacts the upper edges or tips of the radial projections of expansion member 206, the surface area in contact between sleeve body 12 and expansion member 206 is reduced, the friction which exists between the inner surface of sleeve body 12 and the outer surface of expansion member 206, thereby, in turn, reducing the resistance to insertion of expansion member 206 into sleeve body 12. As such, the amount of force required to distally advance expansion member 206 through sleeve body 12 of dilation assembly 102 is reduced.

Figure 29A:
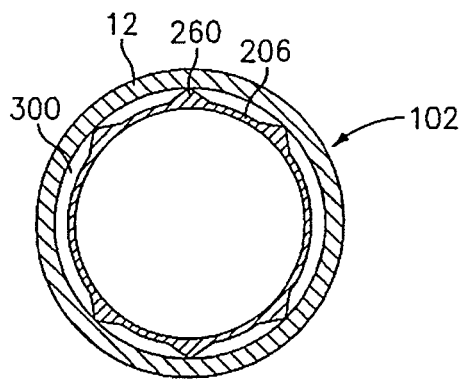
FIG. 29A is a cross-sectional view, taken along A-A of FIG. 24A, of the access and medicament delivery system after the expansion assembly of FIG. 24A has been inserted into the dilation member of the expandable dilation assembly.
Figure 29B:
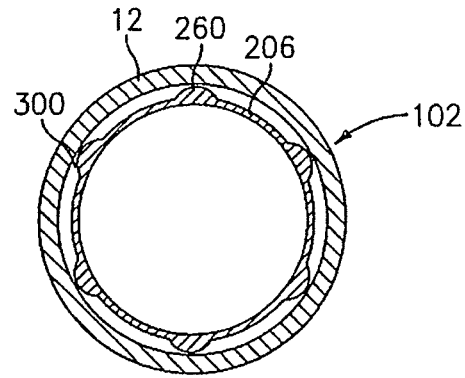
FIG. 29B is a cross-sectional view, taken along B-B of FIG. 24C, of the access and medicament delivery system after the expansion assembly of FIG. 24C has been inserted into the dilation member of the expandable dilation assembly.

As seen in FIGS. 29A and 29B, ribs 260 cause the inner surface of sleeve body 12 to tent up or be spaced a radial distance from the outer surface of expansion member 206. Ribs 260 further define a plurality of longitudinally extending channels 300 around the periphery of expansion member 206 when expansion member 206 is in place within dilation assembly 102. Each channel 300 is bound by the outer surface of expansion member 206, the inner surface of sleeve body 12 and a pair of adjacent ribs 260. As will be described in greater detail below, it is contemplated that the access and medicament delivery system according to the present disclosure can be configured to deliver or inject a medicament "M", through channels 300, into the abdominal cavity of the patient.

Figure 29C:
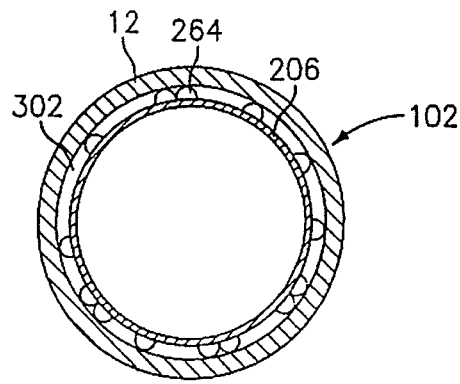
FIG. 29C is a cross-sectional view, taken along C-C of FIG. 24E, of the access and medicament delivery system after the expansion assembly of FIG. 24E has been inserted into the dilation member of the expandable dilation assembly.

Referring to FIG. 29C, bumps 264 act to space the inner surface of sleeve body 12 a radial distance away from the outer surface of expansion member 206. Bumps 264 reduce the contact area between the inner surface of sleeve body 12 and the outer surface of expansion member 206. Since the inner surface of sleeve body 12 only contacts the tips of bumps 264, the contact surface between the inner surface of sleeve body 12 and the outer surface of expansion member 206 is reduced, thus reducing the amount of force required to distally advance expansion member 206 through sleeve body 12. Bumps 264 further act to define a single annular channel 302 surrounding the entire periphery of expansion member 206. It is contemplated that the access and medicament delivery system according to the present disclosure can be adapted to deliver or inject medicament "M" to the abdominal cavity through annular channel 302.

Figure 29D:
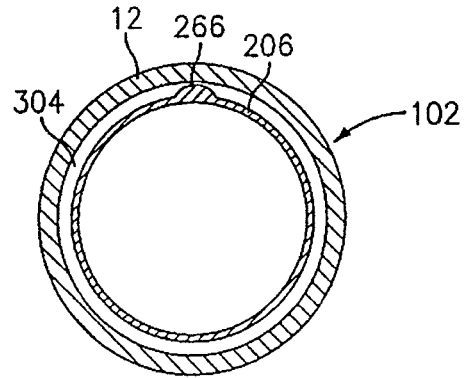
FIG. 29D is a cross-sectional view, taken along D-D of FIG. 24G, of the access and medicament delivery system after the expansion assembly of FIG. 24G has been inserted into the dilation member of the expandable dilation assembly.

Referring now to FIG. 29D, helical thread 266 acts to space the inner surface of sleeve body 12 a radial distance away from the outer surface of expansion member 206. Helical thread 266 reduces the contact area between the inner surface of sleeve body 12 and the outer surface of expansion member 206. Since the inner surface of sleeve body 12 only contacts the upper edge of helical thread 266, the contact surface between the inner surface of sleeve body 12 and the outer surface of expansion member 206 is reduced, the amount of force required to distally advance expansion assembly 204 through sleeve body 12 is reduced. Moreover, helical thread 266 aids in the distal advancement of expansion assembly 204 through sleeve body 12. It is contemplated that an expansion assembly 204 having an expansion member 206, with at least a single helical thread formed thereon, is distally advanced through sleeve body 12 by simply rotating expansion assembly 204 around axis "X" (as seen in FIG. 26) in a screw type action thereby allowing helical threads 266 to draw expansion assembly 204 distally through sleeve body 12. Helical thread 266 further acts to define an annular channel 304 surrounding the entire periphery of expansion member 206. It is contemplated that the access system according to the present disclosure can be adapted to deliver or inject medicament "M" to the abdominal cavity through annular channel 304.

As can be appreciated from FIG. 24I, ribs 268 preferably act to direct, angle and/or channel medicament "M" through channels 269 and distally along the outer surface of expansion member 206.

While any number of ribs 260, 268, bumps 264 or helical threads 266 can be provided on the outer surface of expansion member 206, it is preferred that the number of ribs 260, 268, bumps 264 or helical threads 266 be limited to as few as necessary in order to keep the contact surface between sleeve body 12 and expansion member 206 at a minimum and thereby keep the resistive forces, due to friction between sleeve body 12 and expansion member 206, to a minimum.

As discussed above, it is further contemplated that channels 300, 302 and 304 can be used to deliver medicament "M" into the abdominal cavity of the patient through the patient's skin "S". After expansion member 206 has been inserted into the abdominal cavity of the patient through dilation assembly 102, channels 300, 302 and 304 provide the surgeon with a passage through which medicament "M" can be injected or delivered into the abdominal cavity of the patient. Preferably, with expansion member 206 in place in dilation assembly 102, valve stem 138 is operatively and fluidly coupled to a source of medicament. The surgeon can then inject a medicament "M" into passage 126 of handle 122 via lumen 139 of valve stem 138, see FIG. 20. Since the proximal end of expansion member 206 is sealed by introducer seal 131 the injected medicament "M" will be forced to travel distally through channels 300, 302 and 304, between expansion member 206 and sleeve body 12, until it exits from the distal end of sleeve body 12, see FIGS. 27 and 28.

It is contemplated that an outer surface of expansion assembly 204 and needle assembly 140 can be provided with needle markings (not shown) to assist the surgeon in determining the approximate depths of the body tissue through which needle assembly 140 and expansion assembly 204 are inserted. By first inserting dilation assembly 102 and needle assembly 140, the surgeon may note the extent to which the distal end of needle assembly 140 is inserted. The noted value of depth then serves as a guide for the depth to which expansion assembly 204 is to be inserted into body tissue proximate needle assembly 140 thereby allowing the surgeon to be cognizant of the depth of expansion assembly 204 during its insertion and providing a safety precaution as to the depth of insertion of expansion assembly 204 into the patients abdominal cavity.

Figure 30:
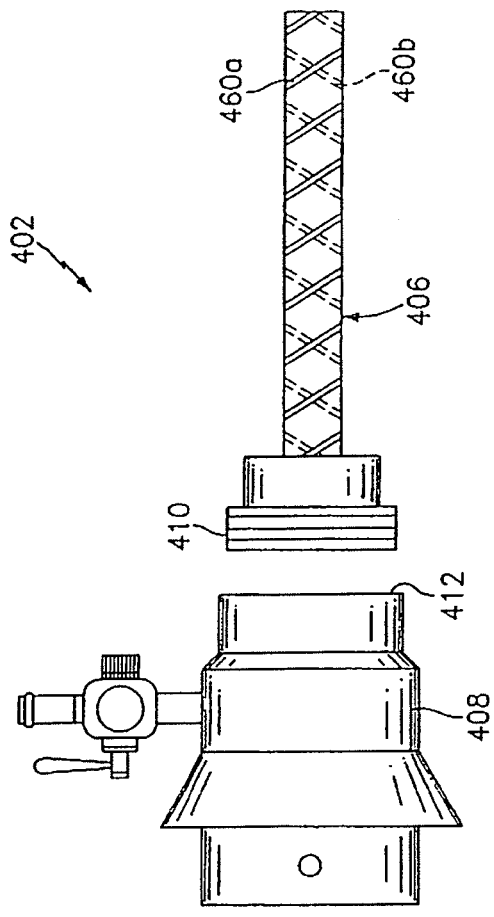
FIG. 30 is a side elevational view of an elongated expansion assembly, partially separated, illustrating an elongated expansion assembly constructed in accordance with an alternative embodiment of the present disclosure.
Figure 31:
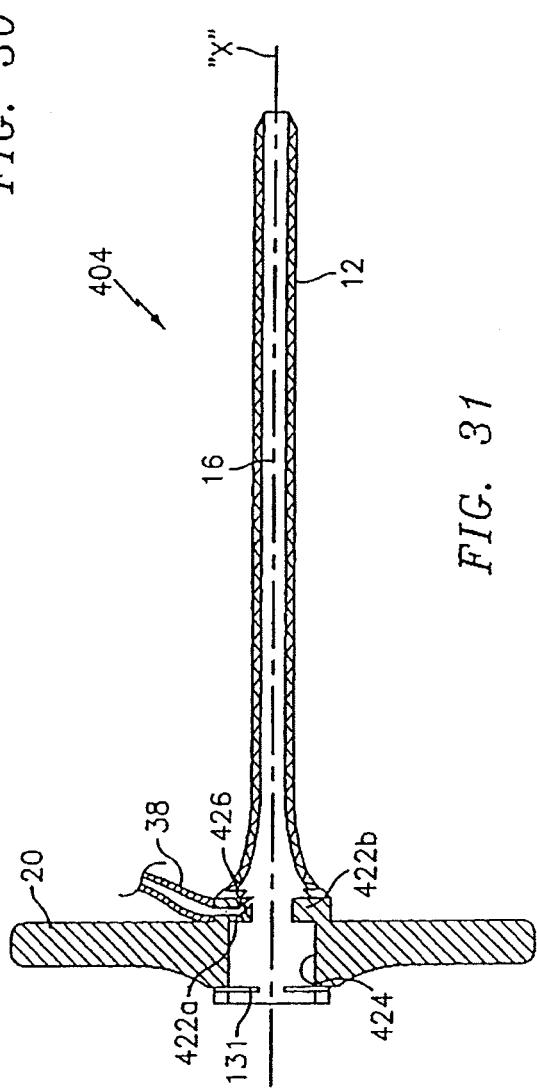
FIG. 31 is a cross-sectional side elevational view, taken along the longitudinal axis, of a radial expandable dilation assembly configured and adapted to be co-operable with the elongated expansion assembly of FIG. 30.
Figure 32:
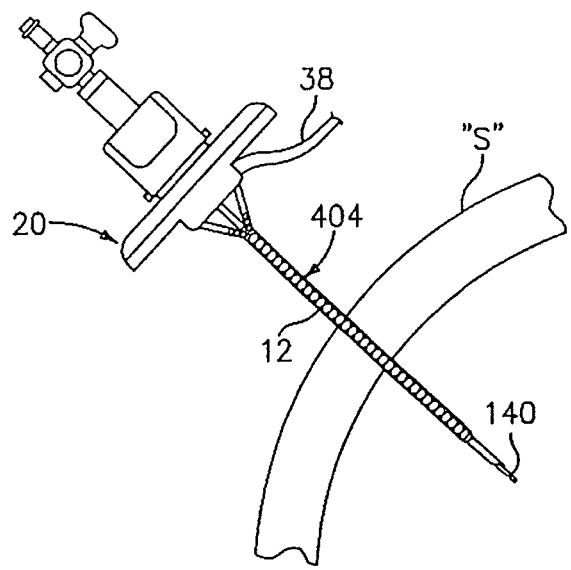
FIGS. 32-35 illustrate use of the access and medicament delivery system using the expansion assembly and expandable dilation assembly of FIGS. 30 and 31.
Figure 33:
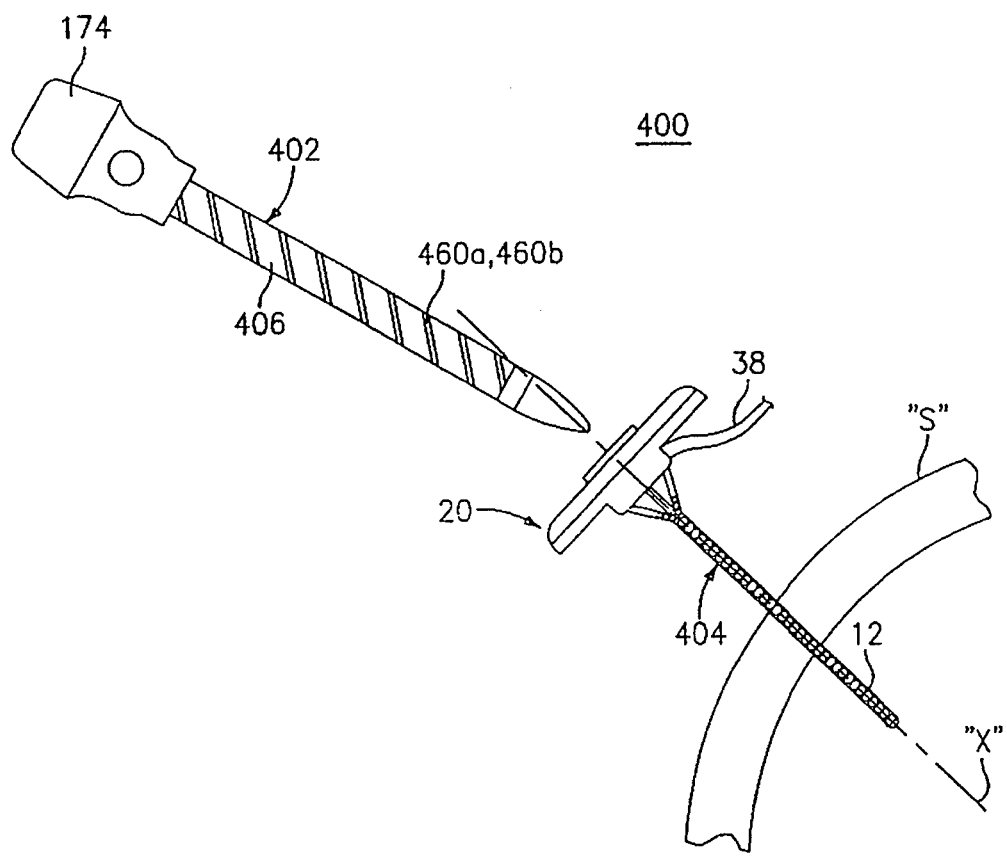

Turning now to FIGS. 30-35, an access and medicament delivery system in accordance with yet another embodiment of the present disclosure, is generally designated 400. Access and medicament delivery system 400 include an expansion assembly 402, as seen in FIG. 30, and a radially expandable dilation assembly 404, as seen in FIG. 31.

As seen in FIG. 30, expansion assembly 402 includes an expansion member 406 and a proximal hub 408. Expansion member 406 includes a threaded connector 410 at its proximal end which can be removably secured to a fitting 412 in the distal end of proximal hub 408. Expansion member 406 defines a second cross-sectional area which is larger than the first cross-sectional area of sleeve body 12. Expansion member 406 is provided with a pair of diametrically opposed helical grooves 460a, 460b formed into an outer surface thereof and extending the entire length thereof.

Referring now to FIG. 31, radially expandable dilation assembly 404 includes a sleeve body 12 and a handle assembly 20, as described above with reference to FIGS. 2-4. In accordance with the present embodiment, as seen in FIG. 31, passage 16 of handle assembly 20 includes a pair of diametrically opposed bosses 422a, 422b extending radially inward from an inner surface 424 thereof. In a preferred embodiment, at least one of the pair of bosses 422a, 422b is provided with a lumen 426 having a proximal portion which opens in a direction substantially radially outward from handle assembly 20 and a distal portion oriented in a direction which opens into the lumen of sleeve body 12. In a preferred embodiment, a valve stem 38 is operatively coupled to handle assembly 20 such that valve stem 38 is in fluid communication with lumen 426.

Each boss 422a, 422b is configured and adapted to be slidably received within and cooperate with a respective helical groove 460a, 460b of handle assembly 20. Preferably, bosses 422a, 422b have a cross-sectional profile which substantially conforms to a cross-sectional profile of helical grooves 460a, 460b. As will be described in greater detail below, bosses 422a, 422b and helical grooves 460a, 460b screwingly cooperate with one another such that expansion assembly 402 is axially advanced through expandable dilation assembly 404 upon a rotation of expansion member 406. Preferably, the distal portion of lumen 426 of each of the pair of bosses 422a, 422b is oriented in a direction substantially co-linear with a pitch of helical grooves 460a, 460b. In this manner, as will be discussed in greater detail below, lumen 426 of one of the pair of bosses 422a, 422b is oriented to deliver a quantity of medicament "M" into and through a respective helical groove 460a, 460b. It is envisioned that each boss 422a, 422b can be provided with a respective lumen 426 configured and adapted to deliver a quantity of medicament "M" into both helical grooves 460a, 460b.

Referring now in detail to FIGS. 32-35, operation of access and medicament delivery system 400, including radially expandable dilation assembly 404 and expansion assembly 402, having the features disclosed above, will be described. Initially, radially expandable dilation assembly 404, having a pneumoperitoneum needle assembly 140 disposed therein, is introduced through the patient's skin "S" (or other body location) by engaging the sharpened distal end of needle assembly 140 against the tissue of the patient's skin "S" and advancing the sleeve/needle assembly forward until sleeve body 12 of dilation assembly 404 extends across the patient's skin "S".

Figure 34:
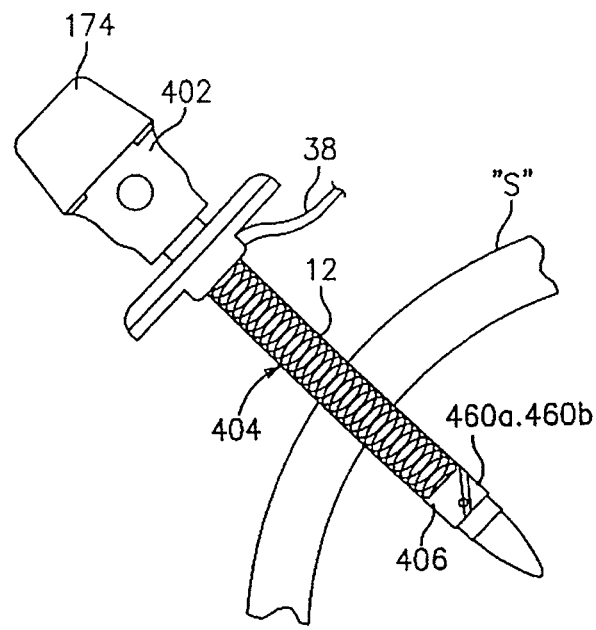
Figure 35:
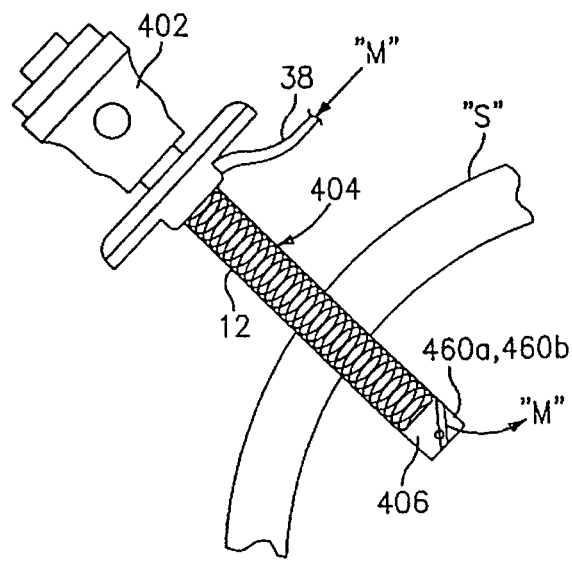

Needle assembly 140 is then removed, and expansion assembly 402 including expansion member 406 and obturator 174, as described above, is introduced into sleeve body 12 of dilation assembly 404, resulting in radial expansion of sleeve body 12, as illustrated in FIGS. 34 and 35. Introduction of expansion assembly 402 into dilation assembly 404 is achieved by aligning the distal end of helical grooves 460a, 460b of expansion member 406 with bosses 422a, 422b of dilation assembly 404 advancing expansion assembly 402 distally until bosses 422a, 422b are received in helical grooves 460a, 460b, firmly holding handle assembly 20 of dilation assembly 404 to prevent rotation and/or proximal movement of dilation assembly 404 in the patient's skin "S", and rotating expansion assembly 402 in a screwing type action, about axis "X", in order to distally draw expansion member 406 and obturator 174 through the patient's skin "S"

and to radially expand dilation assembly 404, from the first cross-sectional area to the second cross-sectional area.

It will be appreciated by those skilled in the art that the insertion of expansion member 406 does not require a force as great as the force required to solely axially insert or thrust expansion assembly 402 into dilation assembly 404. In addition, it should be appreciated that the surgeon will have better control of the depth of insertion of expansion assembly 402 as compared to when the surgeon suddenly thrusts an expansion assembly into dilation assembly 404.

As illustrated in FIG. 35, obturator 174 is then removed from expansion member 406, leaving an access lumen through the patient's skin "S" for the introduction of a variety of other surgical instruments therethrough.

In a preferred method of use, helical grooves 460a, 460b of expansion member 406 are used to deliver medicament "M" into the target surgical site through the patient's skin "S". After expansion member 406 has been inserted through the patient's skin "S", through dilation assembly 404, helical grooves 460a, 460b provide the surgeon with an access channel through which medicament "M" can be injected into the target surgical site of the patient.

With expansion member 406 in place, valve stem 38 is fluidly coupled to a source of medicament (not shown). The surgeon then injects medicament "M" through valve stem 38, through lumen 426 of at least one boss 422a, 422b, distally through respective helical grooves 460a, 460b, out the distal end of helical grooves 460a, 460b and into the target surgical site as needed. Medicament "M" is delivered through an access channel defined by the surfaces of helical grooves 460a, 460b and an inner surface of sleeve body 12 of expandable dilation assembly 404. Since introducer seal 131 creates a fluid-tight seal around expansion member 406, at a location proximal of bosses 422a, 422b, medicament "M" will be forced to travel distally through helical grooves 460a, 460b until it exits from the distal end of sleeve body 12. Alternatively, since bosses 422a, 422b have a cross-sectional profile which conforms to the cross-sectional profile of helical grooves 460a, 460b, bosses 422a, 422b act as stops which prevent medicament "M" from traveling in a proximal direction along expansion member 406.

In the preferred embodiment, a pair of diametrically opposed bosses 422a, 422b have been disclosed, however, it is envisioned that a single boss 422a or 422b can be used. It is further envisioned that passage 16 of handle assembly 20 can be provided with either a single helical thread or a pair of diametrically opposed helical threads (not shown) configured and adapted to engage and be received in either one of or the pair of helical threads 460a, 460b. Further, while a lumen extending through at least one boss 422a, 422b is preferred, it is envisioned that valve stem 38 can open directly into passage 126 of handle assembly 20.

While the above is a complete description of the preferred embodiments of the invention, various alternatives, modifications, and equivalents may be used. Therefore, the above description should not be taken as a limitation to the scope of the invention which is defined by the appended claims.

The invention claimed is:

1. A method of forming and enlarging a percutaneous penetration, the method comprising the steps of: providing a radially expandable dilation assembly having a needle assembly removably inserted in an axial lumen thereof, the radially expandable dilation assembly having a radially expandable sleeve body defining a lumen and an introducer seal disposed across the lumen and defining an opening formed therein, wherein the dilation assembly includes at least one engaging member integrally formed with a handle portion and projecting radially inward; penetrating the radially expandable dilation assembly and needle assembly through tissue to a target surgical site; withdrawing the needle assembly from the radially expandable dilation assembly; and inserting an expansion assembly through the opening formed in the introducer seal and into the axial lumen of the radially expandable dilation assembly, wherein the expansion member includes at least one engaging element formed in an outer surface thereof for co-operable engagement with a respective one of the at least one engaging member of the dilation assembly, wherein the at least one engaging member of the dilation assembly cooperates with the at least one engaging element of the expansion member to axially advance the expansion member through the dilation assembly upon rotation of the expansion member relative to the dilation assembly.

2. The method according to claim 1, wherein the radially expandable dilation assembly includes a handle assembly operatively coupled to a proximal end of the sleeve body, the handle assembly defines an aperture formed therein, and wherein the sleeve body is made up of a radially expandable tubular braid.

3. The method according to claim 2, wherein the sleeve body includes a polymeric layer encasing the tubular braid.

4. The method according to claim 3, wherein the dilation assembly includes a valve stem operatively coupled to the handle portion, the valve stem defining an injection lumen extending into the aperture formed in the handle portion.

5. The method according to claim 4, wherein the polymeric layer includes at least one radially oriented delivery hole formed therein.

6. The method according to claim 5, wherein the seal forms a fluid-tight seal around the expansion member upon insertion of the expansion member into the radially expandable dilation assembly.

7. The method according to claim 6, further including the step of injecting a fluid into the aperture of the handle portion after the expansion member is inserted into the dilation assembly, wherein the seal prevents the fluid from escaping from the proximal end of the dilation assembly and forces the fluid to flow distally through the dilation assembly.

8. The method according to claim 7, wherein the expansion member includes at least one radially projecting element provided on the outer surface thereof, wherein the at least one radially projecting element tents the sleeve body radially outward upon insertion of expansion member through the handle portion and into the sleeve body of the dilation assembly, wherein the radially projecting element defines at least one channel extending along the length of the expansion member when the expansion member is inserted in the dilation assembly, whereby the fluid flows along the at least one channel when the fluid is injected into the aperture of the handle portion.

9. The method according to claim 1, wherein the engaging elements of the expansion assembly include at least one helical groove formed in an outer surface of the expansion member.

10. The method according to claim 9, further including the steps of: coupling the engaging member of the handle portion with the helical groove of the expansion member; and rotating the expansion member relative to the dilation assembly in order to axially advance the expansion member through the dilation member.

11. The method according to claim 10, wherein the fluid is injected through at least one of the engaging members into the corresponding helical groove such that the fluid flows out the distal end of the sleeve body via the helical groove.

* * * * *